(12) United States Patent
Erbe et al.

(10) Patent No.: US 10,251,976 B2
(45) Date of Patent: Apr. 9, 2019

(54) BONE MATRIX COMPOSITIONS AND METHODS FOR THEIR PREPARATION AND USE

(71) Applicants: Erik Erbe, St. Louis, MO (US); Scott Walsh, Jupiter, FL (US); Russel Adams, San Antonio, TX (US)

(72) Inventors: Erik Erbe, St. Louis, MO (US); Scott Walsh, Jupiter, FL (US); Russel Adams, San Antonio, TX (US)

(73) Assignee: Stability Biologics, LLC, Nashville, TN (US)

( * ) Notice: Subject to any disclaimer, the term of this patent is extended or adjusted under 35 U.S.C. 154(b) by 0 days.

(21) Appl. No.: 15/257,281

(22) Filed: Sep. 6, 2016

(65) Prior Publication Data

US 2018/0085491 A1    Mar. 29, 2018

Related U.S. Application Data

(60) Provisional application No. 62/214,603, filed on Sep. 4, 2015.

(51) Int. Cl.
| | | |
|---|---|---|
| *A61L 27/36* | (2006.01) | |
| *A61L 27/54* | (2006.01) | |
| *A61L 27/12* | (2006.01) | |
| *A61L 27/46* | (2006.01) | |

(52) U.S. Cl.
CPC .......... *A61L 27/3608* (2013.01); *A61L 27/12* (2013.01); *A61L 27/3683* (2013.01); *A61L 27/46* (2013.01); *A61L 27/54* (2013.01); *A61L 2300/414* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 8,497,236 B2 * | 7/2013 | Benedict | A61L 27/24 424/423 |
| 2009/0270527 A1 * | 10/2009 | Lin | A61K 6/08 523/116 |
| 2011/0008460 A1 * | 1/2011 | Riman | C01B 25/32 424/602 |

FOREIGN PATENT DOCUMENTS

WO    WO 2010/092001    *  8/2010

OTHER PUBLICATIONS

Malinin et al. "Particulate Bone Allograft Incorporation in Regeneration of Osseous Defects; Importance of Particle Sizes".2007.*

* cited by examiner

*Primary Examiner* — Robert A Wax
*Assistant Examiner* — Danah Al-Awadi
(74) *Attorney, Agent, or Firm* — C. John Brannon; Brannon Sowers & Cracraft PC

(57) ABSTRACT

The present disclosure provides novel bone matrix (BM) materials, and methods for preparation and use of the demineralized bone matrix materials and compositions therefrom. The methods of preparation include the use of a closed-vessel demineralization system, as well as simple, easily reproducible process steps, and significantly shortened times for demineralization. These novel BM materials do not require the inclusion of carriers and/or delivery agents, or the addition of binders, and can be made in various forms, including a clay, putty, crush, powder, or gel. The novel BM compositions and methods disclosed herein may, illustratively, have applications in the medical field, such as in surgical bone graft applications, in the repair and/or regeneration of bone and bone-related tissue, and the like.

13 Claims, 34 Drawing Sheets
Specification includes a Sequence Listing.

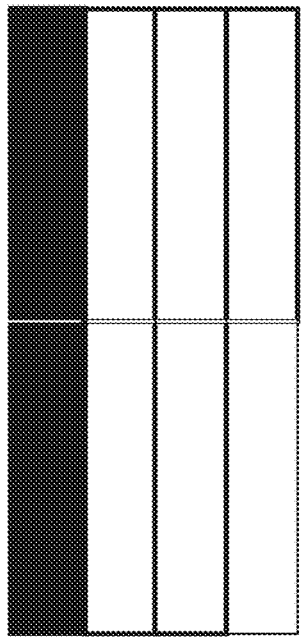
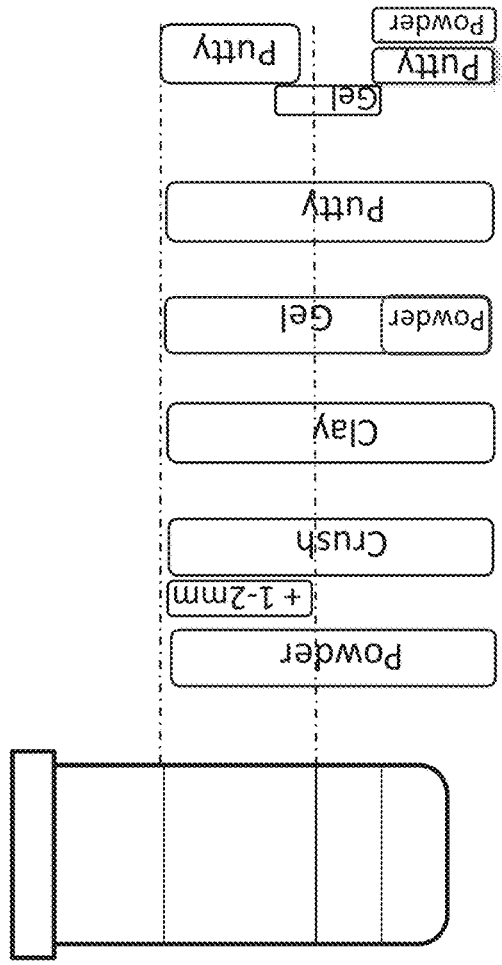
Fig. 3

CVDS Run Summary Table

| DBM Run # | Run Date 2015 | Bone Used (g) | PSD (1/2) | 1N HCl volume (L) | RPM | [K₂K] (%) | Volume of K₂K (L) | Demin. time @55°C | Drying Method | Residual Ca %* | Comments |
|---|---|---|---|---|---|---|---|---|---|---|---|
| 5 | | | | | | | | | | | |
| | 18Feb | 450g | 1 | 4.5L | ~800 | 10% | 12L | 1 hr | Air dried to powder | 7.31% | Required week gel time to inject |
| | 19Feb | 420g | 1 | 4.3L | ~800 | 10% | 20L | 1 hr | Hot plate | 5.97% | Supernatant not collected |
| | 24Mar | 963.93g | 1 | 5.5L | ~1000 | 50% | 8L | 1hr23" | Thermo Incubator | 5.91% | Collected supernatant in 2L beakers |
| | 7April | 1150g | 1 | 5.5L | >1000 | 50% | 10L | 2 hr | FC Oven | 10.9% | First Run to exceed 10:1 Ratio |
| | 27April | 458.2g | 1 | 5.5L | >1000 | 50% | 10L | 1hr30" | FC Oven | 5.52% | First Run arrest in bucket |
| | 29April | 574.2g | 1 | 5.5L | >1000 | 50% | 10L | 1hr30" | FC Oven | 7.83% | Putty Validation run |
| | 11May | 541.0g | 2 | 5.5L | >1000 | 50% | 10L | 1hr30" | FC Oven | 7.85% | Gel+Powder Validation Run |
| | 9June | 289.7g | 1 | 4L | >1000 | 50% | 12L | 1hr30" | Centrifuge | 5.42% | Clay Validation Run |
| | | | | | | | | | | 4.22% | First run with Centrifuge |

Fig. 6

CVDS Characterization Summary Table:
Putty/Clays

| Sample | Mineral Content | Hydroxyapatite Ca₅(PO₄)₃(OH) | Brushite CaHPO₄·2H₂O | Monetite CaHPO₄ | Sylvite KCl | Archerite KH₂PO₄ | Halite NaCl | Residual Calcium | Injectable? | Bone used (g) | Acid Used (L) | Demin Time (hrs) |
|---|---|---|---|---|---|---|---|---|---|---|---|---|
| R5 | 53.91% | NM | NM | NM | NM | NM | NM | 3.98% | yes | 350g | 3.75L | 1 hour |
| R7 | 53.09% | NM | NM | NM | NM | NM | NM | 7.31% | yes | 420.2g | 4.2L | 1 hour |
| R8 | 58.64% | 15.89% | 39.24% | 33.49% | 0.61% | 10.77% | 0% | 5.91% | yes | 420g | 4.3L | 1 hour |
| R9 | 61.81% | 6.07% | 47.16% | 37.52% | 3.10% | 6.15% | 0% | 10.90 | yes | 963.93g | 5.5L | 1 hour 23 minutes |
| V1-R10 | 55.40% | 4.71% | 55.12% | 25.37% | 3.05% | 11.75% | 0% | 7.43% | yes | 1150g | 5.5L | 2 hours |
| V3-R12 | 62.65% | 7.20% | 15.8% | 50.66% | 0.86% | 25.49% | 0% | 7.83% | no | 458.2g | 5.25L | 1 hour 30 minutes |
| DA-1 Putty | 64.57% | 7.26% | 35.79% | 24.49% | 7.07% | 6.78% | 18.61% | 5.42% | yes | 541.0g | 5.25L | 1 hour 30 minutes |
|  |  |  |  |  |  |  |  | 4.22% | yes | 289.7g | 4L | 1 hour 30 minutes |

Fig. 7

CVDS Characterization Summary Table:
Gels

| | | | | | | | | | | |
|---|---|---|---|---|---|---|---|---|---|---|
| R8 White | 71.67% | 1.69% | 74 % | 17% | 0% | 0% | 11.1% | NM | 963.93g | 5.5L | 1 hour 23 minutes |
| R9 White | 75.12% | 6.50% | 29.81% | 41.97% | 6.46% | 15.26% | 0% | 6.8% | Yes | 1150g | 5.5L | 2 hours |
| R8 Cream | 57.90% | 5.17% | 74.77% | 20.05% | 0% | 0% | 0% | 10.4% | NM | 963.93g | 5.5L | 1 hour 23 minutes |
| R9 Cream | 51.25% | 6.65% | 48.35% | 37.02% | 2.13% | 5.38% | 0% | 5.59% | Yes | 1150g | 5.5L | 2 hours |
| V2 Gel | 62.69% | 4.13% | 59.74% | 19.47% | 6.11% | 10.54% | 0% | 7.85% | no | 574.2g | 5.25L | 1 hour 30 minutes |

Fig. 8

CVDS Characterization Summary Table

Powders

| Sample | Mineral Content | Hydroxyapatite Ca₅(PO₄)₃(OH) | Brushite CaHPO₄·2H₂O | Monetite CaHPO₄ | Sylvite KCl | Archerite KH₂PO₄ | Halite NaCl | Residual Calcium | Injectable? | Bone used (g) | Acid Used (L) | Demin Time (hrs) |
|---|---|---|---|---|---|---|---|---|---|---|---|---|
| V2 Powder | 38.04% | 14.9% | 20.77% | 46.86% | 0.6% | 16.82% | | 5.97% | Yes | 450g | 4.5L | 1 hour |
| R8 Pulp | 50.09% | 50.70% | 10.38% | 38.89% | 0% | 0% | 0% | 3.21% | no | 574.2g | 5.25L | 1 hour 30 minutes |
| | | | | | | | | 10.9% | no | 963.93g | 5.5L | 1 hour 23 minutes |
| R9 Pulp | 47.64% | 23.13% | 33.56% | 48.86% | 0% | 6.03% | 0% | 5.36% | no | 1150g | 5.5L | 2 hours |

Fig. 9

| R8 | Hydroxyapatite $Ca_5(PO_4)3(OH)$ | Brushite $CaHPO_4 \cdot 2(H_2O)$ | Monetite $Ca(HPO_4)$ |
|---|---|---|---|
|  |  |  |  |
|  |  |  |  |
|  |  |  |  |

| R9 | Hydroxyapatite $Ca_5(PO_4)3(OH)$ | Brushite $CaHPO_4 \cdot 2(H_2O)$ | Monetite $Ca(HPO_4)$ |
|---|---|---|---|
|  |  |  |  |
|  |  |  |  |
|  |  |  |  |

Fig. 10

CVDS Mineralization Summary Table:

| | Sample | Hydroxyapatite $Ca_5(PO_4)_3(OH)$ | Brushite $CaHPO_4 \cdot 2(H_2O)$ | Monetite $Ca(HPO_4)$ | B/M | Injectability? |
|---|---|---|---|---|---|---|
| Putty | R8 | 15.89% | 39.24% | 33.49% | 1.171 | yes |
| | R9 | 6.07% | 47.16% | 37.52% | 1.25693 | yes |
| | V1-R10 | 4.71% | 55.12% | 25.37% | 2.172 | no |
| | V3-R12 | 7.20% | 15.8% | 50.66% | 0.421109 | yes |
| | DA-1 | 7.26% | 35.79% | 24.49% | 1.46 | Yes |
| | R14 | 13.8% | 36.15% | 39.45% | 0.916 | Yes |
| Gels | R8 White | 1.69% | 74 % | 17% | 1.972281 | NM |
| | R9 White | 6.50% | 29.81% | 41.97% | 0.79451 | Yes |
| | R8 Cream | 5.17% | 74.77% | 20.05% | 1.992804 | NM |
| | R9 Cream | 6.65% | 48.35% | 37.02% | 1.288646 | Yes |
| | V2 Gel | 4.13% | 59.74% | 19.47% | 1.592217 | no |
| Powders | R6 Powder | NM | NM | NM | NM | Yes |
| | V2 Powder | 14.9% | 20.77% | 46.86% | 0.44323 | no |
| | R8 Pulp | 50.70% | 10.38% | 38.89% | 0.276652 | no |
| | R9 Pulp | 23.13% | 33.56% | 48.86% | 0.894456 | no |

Fig. 11

| | Mineral Content (%) | XRD | Residual Calcium Content | Gelation Time | Drying Method | Injectable | Residual Moisture range | Crystal Length |
|---|---|---|---|---|---|---|---|---|
| R4 putty | 46.3% | nm | 8.98% | | Hot Plate | Yes | 47-49.5% | nm |
| R5 putty | 53.91% | nm | 7.31% | 10 days @ 4°C in Bulk | Hot Plate | Yes | 48-51% | nm |
| R6 powder | 39.17% | nm | 5.97% | N/A | Air Dried | Yes after rehydration | 27-33.6% | nm |
| R7 putty | 53.09% | nm | 5.91% | | Hot Plate | Yes | 42%-50.2% | nm |
| R8 W | 71.60% | 17% Monetite 74% Brushite 1.69% Hydroxyapatite | 11.1% | 2 weeks @ room temp | St. Louis Incubator @ 37.5°C | nm | nm | nm |
| R8 C | 57.90% | 74.77% Brushite 5.17% Hydroxyapatite 20.05% Monetite | 10.4 | 2 weeks @ room temp | St. Louis Incubator @ 37.5°C | nm | nm | nm |
| R8 P | 50.03% | 38.89% Monetite 10.38% Brushite 50.7% Hydroxyapatite | 10.90 | 2 weeks @ room temp | St. Louis Incubator @ 37.5°C | nm | nm | nm |
| DBM R8 Putty | unknown | nm | unknown | 2 weeks @ room temp | St. Louis Incubator @ 37.5°C | Yes | 55-38% | nm |
| R9 W | 75.12% | nm | 3.42% | nm | San Antonio FC Oven | Yes | nm | nm |
| R9 C | 51.25% | nm | 5.55% | nm | San Antonio FC Oven | Yes | nm | nm |
| R9 P | 47.64% | nm | 5.36% | nm | San Antonio FC Oven | No | nm | nm |
| DBM R9 Putty | unknown | nm | 5.52% | nm | San Antonio FC Oven | Yes | 55-38% | nm |
| V1 putty | 55.45% | 74.77% Brushite 6.02% Hydroxyapatite 15.2% KHPO4 4.6% sylvite | 7.83% | nm | San Antonio FC Oven | No | 36.8-32.2% | nm |
| V2 pulp | 39.83% | 20.77% Brushite 48.86% Monetite 14.9% Hydroxyapatite 16.82% KHPO4 0.6% sylvite | 3.89% | nm | San Antonio FC Oven | No | nm | nm |
| V2 gel | 62.69% | 73.87% Brushite 16.25% KHPO4 9.8% sylvite | 7.85% | nm | San Antonio FC Oven | No | 26.2-30.2% | nm |

Fig. 12

Results from Calcium Analysis of Validation Runs

| DBM Sample name | Run #1 µg/L of Ca²⁺ detected | Run #2 µg/L of Ca²⁺ detected | Run #3 µg/L of Ca²⁺ detected | Residual Calcium content (n=3)* | RM% for an 8% [Ca²⁺] |
|---|---|---|---|---|---|
| DBM V1-R10 "Putty" | | | | 7.83% | 44% |
| | 1580 | 1641 | 1683 | 3.89% | N/A |
| | 9127 | 9290 | 9478 | 7.85% | 39% |

Fig. 13

A= Brushite optical microscope  B= Monetite optical microscope
C= Brushite SEM image  D= Monetite SEM image SB15-009 Ground Cortical Bone

Run Summary
| DBM Run # | Run Date | Bone Used (g) | PSD (1 or 2) | 1N HCl volume (L) | RPM | [K₂K] (M) | Volume of K₂K (L) | Demin. time /Temp (°C) | Drying Method | Residual Ca % * |
|---|---|---|---|---|---|---|---|---|---|---|
| DA-1 | 9Jun15 | 289.7 | 1 | 4.25L | ~1000 | 0.5M | 12L | 1 hour 30minutes/ 55°C | FC Oven+Centrifuge | 4.22% |
Fig. 33
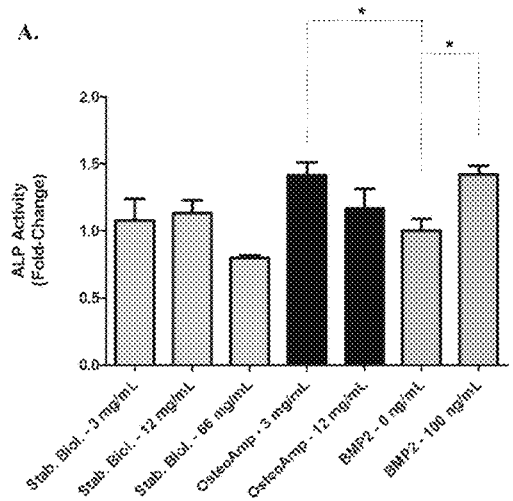
Fig. 34A
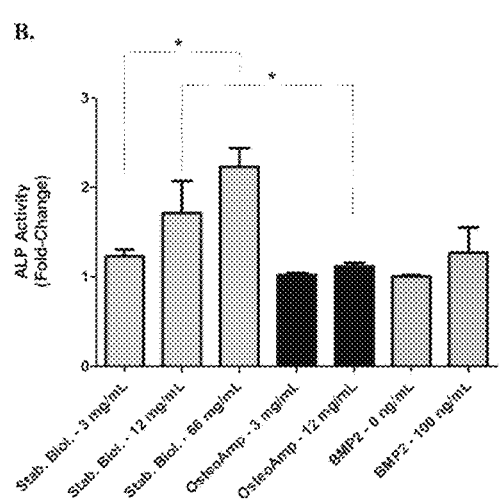
Fig. 34B

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gggacccgct gtcttctagt                                                   20

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tcaactcaaa ttcgctgagg ac                                                22

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aacccagaca caagcattcc                                                   20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gagagcgaag ggtcagtcag                                                   20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctcaacacgg gaaacctcac                                                   20
```

```
<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgctccacca actaagaacg                                                   20
```

BONE MATRIX COMPOSITIONS AND METHODS FOR THEIR PREPARATION AND USE

CROSS-REFERENCE TO RELATED APPLICATIONS

This application claims priority to U.S. Provisional Patent Application No. 62/214,603, filed Sep. 4, 2015.

SEQUENCE LISTING

The instant application contains a Sequence Listing which has been submitted electronically in ASCII format and is hereby incorporated by reference in its entirety. Said ASCII copy, created on Dec. 5, 2017, is named 649-13079_SL.txt and is 1,655 bytes in size.

FIELD OF INVENTION

The present disclosure relates to the field of mammalian tissue engineering and regeneration, in particular as applied to bone and bone-related tissue. More specifically, the present disclosure relates to novel precursor (mineralized and demineralized) bone matrices, and to methods for preparation and use of the bone matrices and compositions therefrom. The novel bone matrix (BM) compositions and methods disclosed herein may, illustratively, have applications in the medical field, such as in surgical bone graft applications, in the repair and/or regeneration of bone and bone-related tissue, and the like.

BACKGROUND OF INVENTION

Rapid and effective repair of bone defects resulting from injury, disease, infection, surgery, aging, tumor, or other pathologic conditions has long been a goal of orthopedic surgery. Over the years, a plethora of compositions and materials have been developed, used and/or proposed for use in the repair of bone defects. The biological, physical, and mechanical properties of these compositions and materials are major factors that influence their suitability and performance in various orthopedic applications.

Millions of bone graft procedures are performed each year worldwide, about half a million of which are performed in the United States alone. Of the latter, approximately a quarter million procedures involve the spine. The bone graft and bone substitute products employed in these procedures may include, for example, bone substitutes, bone dowels, bone matrix (BM) products, tissue engineered matrices, and other allograft precursor bone materials.

Mammalian bone tissue is known to contain one or more proteinaceous materials, presumably active during growth and natural bone healing, that can induce a developmental cascade of cellular events resulting in endochondral and intramembranous bone formation. The active factors have been exchangeably referred to in the literature by various terms including bone morphogenetic or morphogenic proteins (BMP), bone inductive proteins, bone growth or growth factors, osteogenic proteins, osteoinductive proteins, or osteoinductive factors. It has been reported that these growth factors modulate the differentiation of progenitor cells into osteoprogenitor cells, which are responsible for bone and cartilage formation. For example, osteoinductive factors are present within the compound structure of bone tissue, including cortical bone tissue, at very low concentrations, e.g., 0.003% usually reported in ng (nanogram) and pg (pictogram) quantities, and direct the differentiation of pluripotential mesenchymal cells into osteoprogenitor cells that form osteoblasts. Proper demineralization of cortical bone exposes the osteoinductive factors, rendering the bone osteoinductive.

Another aspect of this invention for bone formation and tissue regeneration relates to physiologic mimicry of biologic scaffolds, microenvironments, proteins, growth factors, precursor minerals that prompt osteogenesis. Cells form bone and seek microenvirons in the implanted vicinity to attach, proliferate and differentiate into bone forming precursors and cells. The healing cascade is governed by the similarity and presence of these bioavailable structures and components. The success of a bone graft is determined by its ability to recruit host cells to the site of the graft and modulate their conversion into bone forming cells such as osteoblasts, to repair the defect. This will depend on the osteoconductive, osteoinductive and osteogenic capabilities of the graft. Currently, autograft bone harvested from the iliac crest is considered the "gold standard" due to its superior osteogenic properties. In addition, an autologous bone graft avoids histocompatibility and infectious disease issues. However, autologous bone is limited in supply, is generally painful to the patient upon harvesting, and may lead to significant donor site morbidity (i.e., it may require additional surgical incisions in the patient, may lead to surgical complications, blood loss and may cause additional patient discomfort, and may ultimately increase patient recovery time). Thus, allograft bone is a logical alternative to autograft bone. However, the allograft bone must be rigorously processed and terminally sterilized prior to implantation to remove the risk of disease transmission or an immunological response. This processing can potentially remove the osteogenic and osteoinductive properties of the graft, leaving only an osteoconductive scaffold. These scaffolds are available in a range of preparations (such as morselized particles and struts) for different orthopaedic applications. Some disadvantages of allograft bone grafts include issues relating to histocompatibility, such as rejection by the recipient's immune system, the potential harboring of infectious agents, and diminished physical characteristics such as poor malleability or mechanical properties (e.g., elasticity, compressibility, resiliency, and the like) due to high calcium and mineral content, much of which is discarded during conventional processing.

Presently available bone graft substitutes developed in the art usually have many of the same disadvantages as outlined above with regard to allograft bone grafts. Bone allograft or synthetic graft substitute products are generally formulated as putty and gel type fillers, designed to be inserted into surgically created or congenital bone defects (i.e., defect or void fillers). Traditionally, bone graft substitutes may be made from allogeneic bone chips, granules, or bone powder, or synthetic materials with or without carrier compositions. Additionally, there are a few xenogeneic bone graft products available that are made from bovine bone. Disadvantages of the xenogeneic bone graft products are similar to those observed with allografts, including potential immune reaction to xenogeneic bone and infectious agents, including prions.

Demineralized Bone Matrices (DBM) is one example of allograft bone that has had the inorganic minerals removed, leaving behind the organic "collagen" matrix. The removal of the bone minerals exposes more biologically active bone morphogenetic proteins and increases the osteoinductivity of the graft, resulting in DBM that has superior biological properties and activity spectrum than undemineralized bone grafts. Conversely the mechanical properties of the DBM are significantly altered and/or diminished.

It has been reported that DBM that is derived from cortical bone is an osteoinductive material, because it induces bone growth when implanted in an ectopic site of a rodent, owing to the osteoinductive factors contained within the DBM. It has also been reported that such DBM contains numerous osteoinductive factors, e.g., BMP 1-15, which are part of the transforming growth factor-beta (TGF-beta) superfamily. Of this family, BMP-2 has become the most important and widely studied of the BMP family of proteins. There are also other proteins present in DBM that are not osteoinductive alone but still contribute to bone growth, including fibroblast growth factor-2 (FGF-2), insulin-like growth factor-I and -II (IGF-I and IGF-II), platelet derived growth factor (PDGF), VEGF (Vascularized Endothelial Growth Factor) promoting angiogenesis, and transforming growth factor-beta 1 (TGF-beta.1).

Currently, there is a range of DBM products approved by the U.S. Food and Drug Administration (FDA) for clinical use as well as regulated under compliance to HCT/P (Human Cell and Tissue Products) guidelines. However, various limitations and quality issues still plague most of the available DBM products, including many of the same disadvantages and practical shortcomings mentioned above in regard to allograft bone products.

One prime limitation with current systems relates to the alteration and degradation of physiologic structures, factors and components during conventional processing. During acid demineralization, most of the Osteogenic growth factors are removed and discard along with the acidic byproducts. The resulting collagen, mineral and protein microstructure is compromised and altered physiologically.

Another disadvantage of current DBM products is that they suffer from poor "wet field integrity," i.e., their inability to remain intact when exposed to wet conditions. Thus, they tend to break up and/or fall apart in wet environments, such as is typically present in a surgical field, wherein blood, buffers, and other water-containing materials are present. Additionally, in such wet environments, current BM products tend to stick to surgeons' gloves while being reshaped and remodeled, creating a mess. Likewise, they tend to wash away partially while the surgical site is undergoing lavage. Another typical additive used by surgeons, i.e. Bone Marrow Aspirate (BMA), growth factors and/or cell preparations, which tend to alter handling deleteriously. To overcome these shortcomings, currently available BM products typically contain various additional materials to aid in holding the BM product together in the wet environment. Thus, binders and polymers are added, such as various poloxamers (nonionic triblock copolymers). It is highly desirable and advantageous, therefore, to provide DBM products that are 100% physiologic (i.e. no carrier) to better absorb growth factors and that exhibit wet field integrity, without the need for inclusion of binders, poloxamers, and the like.

Moreover, many currently available BM products even with addition of other factors are limited in their use by the need to add to them various carriers and delivery agents to facilitate their handling, injection, and implantation. Typical carriers include materials such as glycerin, carboxymethyl cellulose (commonly known as "CMC"), polymers (e.g. polaxomers) and the like. It is highly desirable and advantageous, therefore, to provide DBM products that are 100% physiologic, without the need to include carriers and delivery agents.

Additionally, many currently available BM products suffer from variability and inconsistency. This shortcoming arises from the fact that many DBM producers carry out their DBM production processes in multi-batch demineralization runs, followed by blending together the various batches.

Accordingly, there is an ongoing need to provide improved DBM products that overcome some or all of the disadvantages and shortcomings of existing DBM products. Likewise, there is an ongoing need to develop practical and economical methods for preparation of the improved DBM products.

Furthermore, there is a need to provide DBM products that are compliant with the standards of the American Association of Tissue Banks (AATB), i.e., having residual $Ca^{+2}$ content <8%. Many current processes for generating DBM products tend to drastically or completely deplete the DBM of all minerals, including some important minerals that are known to possess osteogenic and osteoinductive properties.

The presently disclosed invention addresses these needs.

BRIEF SUMMARY OF INVENTION

In one embodiment, disclosed herein are novel BM bone graft products. These BM bone graft products are fully compliant with the FDA's regulations pertaining to human cells, tissues, and cellular and tissue-based products (i.e., HC/P regulations). In one aspect, the DBM bone graft products are comprised of human demineralized bone matrix. In another aspect, the BM bone graft products comprise compositions that do not require the inclusion of additional materials such as carriers or delivery agents. The DBM bone graft products herein come in a variety of physical forms, including, but not limited to, a paste form that is typically injectable through a syringe (illustratively, a 1 ml, 5 ml, 10 ml or 20 ml syringe), a putty that is moldable like a clay and placed into a surgical site by the clinician, as a crunch form that behaves like the paste with the addition of larger (e.g., 1 to 4 mm) chunks of mineralized cancellous bone, or as a gel. In addition to the above forms, the DBM bone graft products herein come in a powder or particulate form (illustratively, 100 to 1000 microns), which may typically be admixed with blood or bone marrow aspirate to form a paste by the clinician. Some characteristics of the DBM bone graft products herein, in addition to the physical forms, include a lowered calcium ion $[Ca^{+2}]$ content, such as <8%, or even <2% in some cases, and preservation in the DBM of sufficient levels of endogenous growth factors (such as, illustratively, BMP-2, BMP-4, BMP-7, VEGF, and the like) in highly bioavailable form to be therapeutically effective. However, additional compositions not under 8% residual $Ca^{+2}$ content are of utility. Physiologic mimicry, including microenvironment, scaffold structure surface and cellular and protein affinity, growth factors, cytokines and proteins supportive of osteogenesis.

One attribute of the DBM bone graft products disclosed herein are that they possess excellent wet field integrity characteristics. The novel products disclosed herein are self-binding, and possess the ability to hold together when being remodeled or reshaped, even though they are free from the typical binders used in other commercially available DBM products. The novel products disclosed herein remain largely intact after injection or placement into the surgical site and when the site is undergoing lavage, as is discussed further below. Additionally, Osteogenic additives (BMA, BMP, cellular constructs) commonly used by surgeons do not significantly alter the handling.

In another embodiment, disclosed herein are methods for preparation of the DBM bone graft products. These methods comprise multi-step processes that may include one or more of the following steps: debriding, cleaning and disinfecting original donor bone; defatting and removal of all lipids, cells and marrow; lyophilizing and drying the bone; and sectioning and comminution of the bone into sized powder. The donor bone may be of various types and sources such as, illustratively, long cortical and/or cancellous bones. The multi-step processes also include the step of admixing a premeasured quantity of comminuted bone powder of a particular particle size distribution (PSD) with a quantity of a mineral acid, such as, illustratively, hydrochloric acid (HCl), acetic acid, combinations and various concentrations under carefully controlled conditions including temperature, time, degree of agitation, and load versus acid volume. Typical acid: particulate ratio of 10:1 are not required by this method. In one aspect, the multi-step processes further include the steps of arresting and extracting all related demineralized powder and proteins, and drying down the mixture into pastes for appropriate handling.

In one aspect, the DBM methods herein are carried out and completed in a significantly shortened period of time relative to the typical times reported in the production of other commercially available DBM products. In another aspect of the methods herein, certain steps of the multi-step processes are performed in a closed vessel demineralization system (CVDS). Some advantages resulting from the use of this CVDS system are preservation of sterility and a lower bio-burden, due to the closed system and the shortened times involved. In another aspect, purity of the resulting DBM bone graft product, preservation of important osteogenic proteins, growth factors, physiologic consistency and preservation, decreasing variability, as well as in situ formation of CaP minerals more conducive to osteogenesis, via osteoconduction and osteoinductive, increased radiodensity for medical imaging and visualization and condition of remnant collagen structures, gelatin are all contingent upon the multiple, yet minimally manipulated, steps in the multi-step process. Additional characteristics of the DBM bone graft product obtained by the methods herein include: a cleaner, "whiter" and more esthetically pleasing product in comparison to other existing DBM products; a product that lends itself to easier handling by the surgeon or technician and reduced stickiness to gloves; a product that does not irrigate or dissolve upon implantation; a product that is easily moldable; a product that possesses consistent formulation in regard to touch with no clumps or chunks; and, a product that can be readily co-mingled with other products, such as, illustratively, bone marrow aspirate (BMA).

Illustratively, the processes herein comprise the steps of treating comminuted bone powder with hydrochloric acid under controlled conditions of temperature, sterility, agitation, and time, arresting the reaction with phosphate buffer, rinsing sequentially with water and acetone, isolation of the DBM, centrifugation under chilled, −5 C conditions, protein capture, preservation, CaP mineral formation (Monetite $CaHPO_4$ and Brushite $CaHPO_4 \cdot 2H_2O$), gelation formation, hydration and drying, e.g., in a forced convection oven. All of these lead to biosimilar physiologic Osteogenic structures.

The novelty, herein, resides in retaining endogenous growth factors, microstructural elements of collagen, gelatin, etc . . . , minerals, all of which mimic the original physiologic bone precursor, osteoid, bone precursor composition and microstructure. Furthermore, the in situ formation of physiologic Ca-deficient mineral species, with respect to HA, of the size, composition and structure conducive for promotion and acceleration of physiologic healing cascade and osteogenesis.

The advantages and desirable features of the present invention will become apparent from the following detailed description, the claims, and the accompanying drawings and figures, as well as from the additional data in the attached addendum.

BRIEF DESCRIPTION OF DRAWINGS

FIG. 3 depicts a BM production run wherein after rinsing the layers were allowed to separate into a bottom "Pulp" layer, a middle "Cream" layer, and an upper "White" layer, as well as the crush, clay, powder, putty, and gel forms that are obtained from the layers.

FIG. 6 is a summary tabular display for all the materials/independent variables controlled during the demineralization process.

FIG. 7 is a tabular display of CVDS characterization of all of the various BM Putties/Clays.

FIG. 8 is a tabular display of CVDS characterization of all of the various BM gels.

FIG. 9 is a tabular display of CVDS characterization of all of the various BM powders.

FIG. 10 is a tabular display showing a comparison of the mineral percentages calculated from x-ray diffraction analysis for the constituents of the two representative BM samples R8 and R9.

FIG. 11 is a tabular display showing a comparison of the mineral percentages calculated from x-ray diffraction analysis for all BM materials.

FIG. 12 is a tabular display of various BM materials.

FIG. 13 shows the results of residual calcium analysis.

FIG. 33 is a table showing a summary of Example 2.

FIG. 34A, B are graphs showing ALP activity.

DETAILED DESCRIPTION

Figure 1:
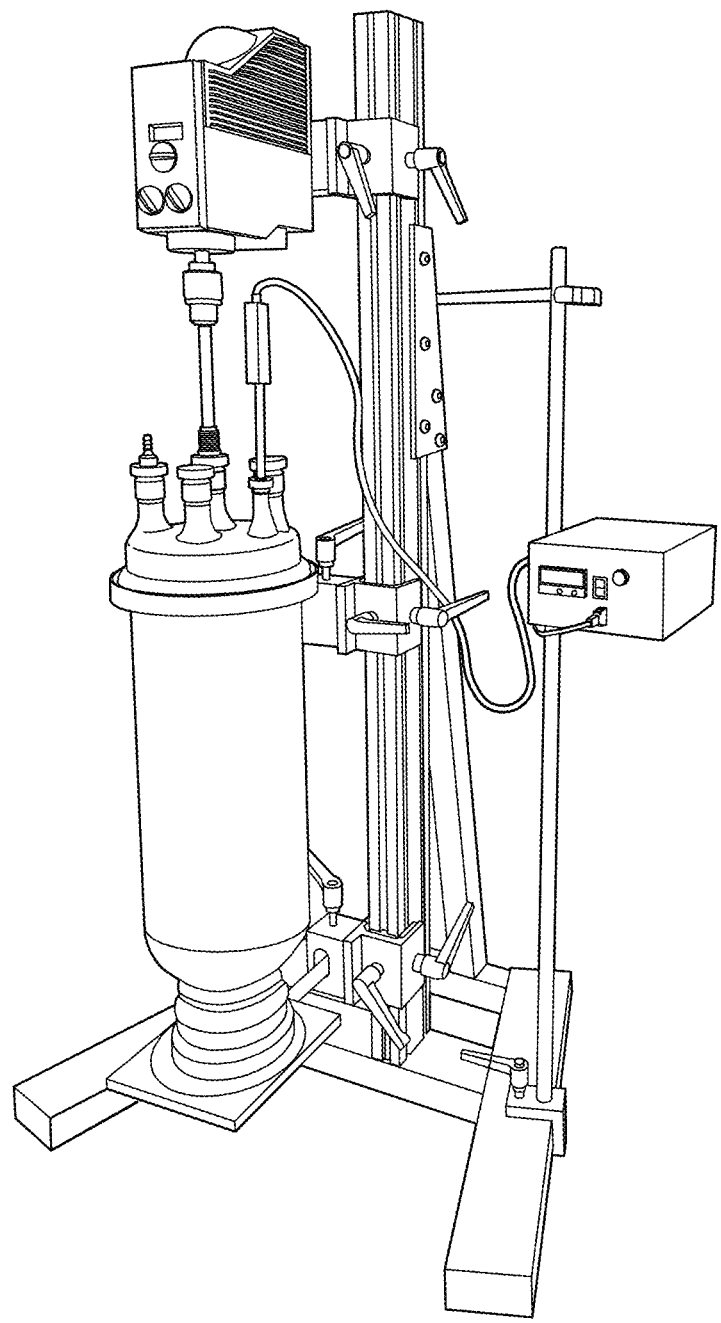
FIG. 1 shows a vessel and associated set-up used herein for demineralizing bone powder.

Before the present methods, implementations and systems are disclosed and described, it is to be understood that this invention is not limited to specific methods, specific components, implementation, or to particular compositions, and as such may, of course, vary. It is also to be understood that the terminology used herein is for the purpose of describing particular implementations only and is not intended to be limiting. Neither are explanations that have been provided to assist in understanding the disclosure meant to be limiting.

As used in the specification and the claims, the singular forms "a," "an" and "the" include plural referents unless the context clearly dictates otherwise. Ranges may be expressed in ways including from "about" one particular value, and/or to "about" another particular value. When such a range is expressed, another implementation may include from the one particular value and/or to the other particular value. Similarly, when values are expressed as approximations, for example by use of the antecedent "about," it will be understood that the particular value forms another implementation. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not. Similarly, "typical" or "typically" means that the subsequently described event or circumstance may or may not occur, and that the description includes instances where said event or circumstance occurs and instances where it does not.

Unless otherwise defined, the technical, scientific, and medical terminology used herein has the same meaning as understood by those skilled in the art. However, for the purposes of establishing support for various terms that are used in the present application, the following technical comments, definitions, and review are provided for reference.

The term "osteoconductive" as used herein refers to a material that facilitates the spontaneous formation of bone by furnishing a microenvironment that supports the ingrowth of blood vessels, perivascular tissue and osteoprogenitor cells into the site where it is deposited The term "osteoinductive" refers to substances within the bone matrix that actively trigger the formation of bone. Osteoinductive material promotes the recruitment of osteoprogenitor cells from an ectopic or an orthotopic site and stimulates their proliferation and differentiation into bone-forming cells, i.e. osteoblasts.

The term "osteogenic" as used herein refers to a substance containing live osteoprogenitor cells in its matrix that actively promote new bone formation.

The term "matrix" as used herein refers to an extracellular matrix of bone remaining after processing and/or demineralization. The highly porous bone precursor matrix provides scaffolding conducive for cell attachment and tissue regeneration.

The term "BMP" as used herein refers to bone morphogenetic proteins that have been associated with bone and cartilage growth through the mechanism of providing signals to osteogenic cells to differentiate, proliferate and regenerate new tissue.

The term "growth factors" as used herein refers to known physiologic proteins, small molecules and hormones that promote neovascularization, angiogenesis and growth of new tissue, as well as osteogenesis.

In one embodiment, the present disclosure describes a method for preparation of a novel BM bone graft composition under CVDS conditions. In one aspect, the method is carried out as a single batch production, thus leading to improved consistency, shortened production times, and large output volumes. The process also leads to greater hydration, volume expansion from starting materials. Additionally, this expansion of the inherent structures serve to increase endogenous protein, growth factor retention and bioavailability. In another aspect, the CVDS conditions described herein lead to simplified product portfolio production by said method comprising a multi-step process that comprises any one or more of the following steps:

(i) placing a quantity of a mineral acid into a reactor vessel;

(ii) heating the mineral acid while stirring at a predetermined stirring rate, 1000+ rpm, until an appropriate temperature is reached;

(iii) adding to the stirred acid a premeasured quantity of bone powder, resulting in a mixture;

(iv) adjusting the stirring rate to a desired speed and continuing to heat the mixture for a predetermined period of time;

(v) discontinuing heating, and adjusting the stirring rate to a desired speed;

(vi) adding to the mixture a pre-chilled quantity of a buffer solution;

(vii) discontinuing stirring and allowing the resultant solids to settle;

(viii) decanting or suctioning the supernatant liquid into one or more secondary containers;

(ix) adding additional buffer solution to each of the one or more secondary containers until a pH≥6 is achieved;

Centrifugation Steps (x) replacing the decanted or suctioned supernatant by adding an additional quantity of pre-chilled buffer into the reactor vessel;

(xi) repeating steps (viii)-(x) until a pH of about ≥6 is achieved;

(xii) after a pH of about ≥6 is achieved, decanting or suctioning the supernatant liquid from the reactor vessel;

(xiii) adding to the reactor vessel a sufficient quantity of deionized or distilled water to dissolve any salts that may have formed during the addition of the buffer to the acid;

(xiv) decanting or suctioning off the supernatant water/salt solution in (xiii) above;

(xv) adding a quantity of acetone into each of the reactor vessel and the one or more secondary containers;

(xvi) allowing sufficient time after acetone addition for precipitates to settle, roughly forming a "white" fluffy upper layer, a middle layer that is a "cream" viscous semi-solid paste, and a bottom layer that is a "tan" pulp-like powder;

(xvii) carefully decanting or suctioning off most of the supernatant acetone solutions in the reactor vessel and secondary containers;

(xviii) carefully separating the three layers from the reactor vessel and secondary containers by pouring like-layers into drying trays;

(xix) allowing residual acetone to evaporate;

(xx) mixing desired quantities from the contents of each drying tray, typically in one or more mixing bowls, until contents appear to be homogenous; and, (xxi) allowing mixed contents to congeal in a refrigerator until the desired rheology is achieved.

A feature of the foregoing multi-step process is that the demineralization steps, i.e., steps (iv) through (vii), are carried out in a closed vessel system. This closed vessel demineralization system (CVDS) offers several advantages, which will become clear in the discussion below. Another feature of the foregoing multi-step process has to do with the high rate of stirring. Without being bound by theory, it is believed that the high rate of stirring generates high shear forces that are believed to contribute to breakup of the bone, collagen, rendering the natural BMP and other osteoinductive and osteogenic contents more bioavailable. Additionally, during the processing, CaP minerals are formed in situ leading to improved Osteogenicity. A third feature of the foregoing multi-step process is that it may optionally, but typically, be carried out under sterile conditions, including, illustratively, a sterile room, sterile vessels and sterile associated equipment, and highly purified starting materials and reagents.

The demineralization 1 acid in step (i) above may be any suitable mineral acid, typically HCl, Acetic acid, EDTA or combinations thereof. The HCl concentration may be in the range of about 0.1N to about 2N, typically in the range of about 0.5N to about 1.5N, and most typically about 1N. The quantity of HCl used may vary. As an illustrative example, in the case where 1N HCl is used, a wt./vol. ratio of bone powder to HCl in the range of about 1/20 to about 2/5 may be used, with a typical ratio of about 1/10.

In step (ii) above, it is typical that stirring be done with a mechanical stirrer, and that an initial stirring rate in the range of about 200 rpm to about 600 rpm be used. Typically, the stirring rate is about 1000+ rpm. The appropriate temperature is one that does not cause denaturing of the bone proteins, such as a temperature in the range of about 35° C. to about 60° C., and typically about 55° C.

In step (iii) above, it is typical that the bone powder be added in portions at such a rate so as to prevent excessive foaming, while gradually increasing the stirring speed until a stirring rate in the range of about 800 rpm to about 1000 rpm is achieved.

In step (iv) above, a typical stirring speed is at a rate in the range of about 800 rpm to about 1200 rpm, and more typically about 1000 rpm. The period of time is any suitable time period in the range of about 0.5 h to about 3 h, and typically in the range of about 1 h to about 2 h.

In step (v) above, a desired stirring speed is at a rate in the range of about 200 rpm to about 600 rpm, and typically about 400 rpm.

In step (vi) above, any suitable buffer may be used, illustratively, a potassium phosphate buffer, such as commercially available $K_2K$ Potassium Phosphate Buffer Solution. The buffer solution may be pre-chilled, for example, to a temperature of about 4° C.; however, as contemplated herein, higher or lower temperatures for the buffer may be used as well if needed.

In steps (vi) and (ix)-(xi) above, the quantity of buffer solution to be added is any quantity that would result in achieving a pH in the range of about 6 to about 7. Measuring the pH of the mixture may be carried out by any suitable pH measuring method known in the art, such as, illustratively, by the use of indicator strips or pH meter.

In step (xiii) above, the deionized or distilled water to be added may typically be pre-chilled, such as, illustratively, to a temperature of about 4° C. Likewise, in step (xv) above, the acetone to be added may typically be pre-chilled, such as, illustratively, to a temperature of about 4° C. However, as contemplated herein, in both steps, higher or lower temperatures may be used as well if needed.

In step (xv) above, the total quantity of acetone used may vary as needed. Illustratively, in the case wherein 1N HCl is used as the mineral acid, the total quantity of acetone used may range from about half the volume of the HCl to about double the volume of the HCl. Typically, the total quantity of acetone used is roughly about the same volume of the HCl used.

In step (xvi) above, as contemplated herein, sufficient time for settling after acetone addition may vary as needed, such as for a time period in the range of 1 h to about 24 h, or longer if needed.

In step (xix) above, as contemplated herein, acetone evaporation may be expedited by heating at such a temperature that does not cause denaturing of the bone proteins. This may be accomplished by using, illustratively, a hotplate or a forced convection oven.

In step (xxi) above, as contemplated herein, the refrigerator temperature may be any suitable temperature such as, illustratively, a temperature of about 4° C.

In another embodiment, the present disclosure describes another illustrative method for preparation of a novel DBM bone graft composition, said method including a multi-step process that comprises any one or more of the following steps:

(a) placing a quantity of a mineral acid into a reactor vessel;

(b) heating the mineral acid while stirring at a predetermined stirring rate, until an appropriate temperature is reached;

(c) adding to the stirred acid a premeasured quantity of bone powder, resulting in a mixture;

(d) adjusting the stirring rate to a desired speed and continuing to heat the mixture for a predetermined period of time;

(e) discontinuing heating and stirring;

(f) pouring reactor vessel contents into a sterile first container;

(g) adding to the contents of the sterile first container a quantity of a buffer solution until a pH of about 6 is achieved;

(h) transferring contents of sterile first container into sterile centrifuge bottles;

(i) placing the sterile centrifuge bottles of step (h) into a centrifuge and centrifuging for a predetermined period of time;

(j) decanting supernatant liquid from centrifuge bottles;

(k) rinsing the remaining pellets in the centrifuge tubes with sterile water, and decanting water layers;

(l) adding to each of the centrifuge bottles a quantity of pre-chilled acetone, shaking vigorously, and decanting the acetone layers;

(m) adding to each of the centrifuge bottles a sufficient quantity of acetone to submerge the pellets therein;

(n) shaking the centrifuge bottles vigorously to obtain a homogenous mixture in each;

(o) pouring contents of the centrifuge bottles in step (n) into one drying tray or multiple drying trays as needed, rinsing interior of centrifuge bottles with additional acetone as needed;

(p) placing the one drying tray or multiple drying trays from step (o) into an oven, and heating the oven at a desirable temperature for a suitable period of time;

(q) transferring contents of drying trays from step (p) into a mixing bowl and mixing to obtain a homogenous putty; and (r) subjecting the putty obtained in step (q) to cooling in a refrigerator to obtain a gel.

In a related embodiment to the foregoing, the present disclosure describes a process for preparing the gel obtained in the preceding paragraph for use or shipping, the process comprising the steps of:

(s) allowing a desired quantity of the gel obtained in step (r) above to thaw to a putty;

(t) transferring the thawed putty obtained in step (s) above into sterile syringes or syringe-like containers;

(u) placing the putty-filled syringes or syringe-like containers obtained in step (t) in sterile packages, and sealing the packages under sterile conditions; and (v) cooling the sealed sterile packages in a freezer to allow the contents to gel, and store therein until ready for use or shipping.

A feature of the foregoing embodiment of the multi-step process is that the demineralization steps, i.e., steps (c) through (e), are carried out in a closed vessel demineralization system (CVDS). This includes the use of a sterile room, sterile vessels and associated equipment, and highly purified starting materials and reagents. The use of CVDS conditions offers several advantages, which will become clear in the discussion below. A second feature of the foregoing multi-step process has to do with the high rate of stirring. Without being bound by theory, it is believed that the high rate of stirring generates high shear forces that are believed to contribute to breakup of the collagen, rendering the natural BMP and other osteoinductive and osteogenic contents more bioavailable. The exact shear rate achieved by a particular stir rate may be calculated for a 6 liter CVDS using a pitched impellor blade using the formula:

$$\gamma = \sqrt{\frac{4N_p \rho d_i^2}{\pi 2^3 \mu}} \cdot N^{3/2}$$

Where $\gamma$ is shear rate in 1/s, Np is the power number (or Newton number), $\rho$ is the density of the fluid, di is the diameter of the impeller, $\mu$ is the viscosity, and N is the agitation speed in 1/s. Over a range of suitable impeller speeds the following shear rates may be produced.

Higher rpm stir rates than those shown in the above table may also be used provided the reaction vessel and stirring equipment is capable of producing such stir rates.

The mineral acid in step (a) above may be any suitable mineral acid, typically HCl. The HCl concentration may be in the range of about 0.1N to about 2N, typically in the range of about 0.5N to about 1.5N, and most typically about 1N. The quantity of HCl used may vary. As an illustrative example, in the case where 1N HCl is used, a wt./vol. ratio of bone powder to HCl in the range of about 1/20 to about 2/5 may be used. Optionally, the HCl may be pre-warmed, e.g., to 37° C.

In step (b) above, it is typically that stirring be done with a mechanical stirrer, and that a stirring rate in the range of about 400 rpm to about 1300 rpm be used. typically the stirring rate is about 800 rpm to about 1100 rpm, and most typically the stirring rate is about 1000 rpm. The appropriate temperature is one that does not cause denaturing of the bone proteins, such as a temperature in the range of about 35° C. to about 60° C., and typically about 55° C.

In step (c) above, it is typically that the bone powder be added at such a rate so as to prevent excessive foaming.

In step (d) above, a desired stirring speed is at a rate in the range of about 800 rpm to about 1200 rpm, and typically about 1000 rpm. The period of time is any suitable time period in the range of about 0.5 h to about 3 h, typically in the range of about 1 h to about 2 h.

In step (f) above, the reactor vessel contents may optionally be poured into a multiplicity of sterile containers instead of a single sterile container.

In step (g) above, any suitable buffer may be used, illustratively, a potassium phosphate buffer, such as $K_2K$ Potassium Phosphate Buffer Solution. The buffer solution may optionally be pre-chilled, for example, to a temperature of about 4° C.; however, as contemplated herein, higher or lower temperatures for the buffer may be used as well if needed.

In step (g) above, measuring the pH of the mixture may be carried out by any suitable pH measuring method known in the art, such as, illustratively, by the use of indicator strips.

In steps (h) and (i) above, optionally the number of centrifuge bottles used may be greater than can be loaded into the centrifuge for a single centrifuging run; as such, the centrifuging step may be done in a multiplicity of batches. Alternatively, multiple centrifuges may be used. In step (i) above, the centrifuging time may be any suitable period of time that allows for separation of the solids, such as, illustratively, a period of time in the range from about 1 h to about 12 h. It is understood that periods of time longer than 12 h may be used if needed.

In step (l) above, a sufficient quantity of acetone may be used; illustrative of a sufficient quantity of acetone is a quantity that merely submerges the pellets in the centrifuge bottles or fills up the bottles to the nape, and any quantity in between. It is typically that the acetone be pre-chilled prior to use.

In step (p) above, it is typically that a fan-assisted convection oven (commonly known as "FC oven") be used. Illustrative of the temperature that may be used is a temperature in the range of from about 28° C. to about 45° C., typically in the range of from 30° C. to about 39° C. It is understood that a lower temperature may initially be used, which then may be gradually raised to a higher temperature. As contemplated herein, the suitable period of time may be in the range of from about 1 h to about 24 h, and typically in the range of from about 8 h to about 16 h. If an FC oven is used, which typically include a damper and a fan speed control means, the initial damper and fan speed settings may be at less than 100%, and may be gradually changed to 100%, especially toward the latter parts of the period of time. The suitable period of time is more typically determined by carrying out periodic moisture analyses on samples withdrawn from the drying trays, as well as by assessing injectability, such as, for example, by trying to inject a sample via a 10 cc syringe. It is desirable that the sample not become too dry to inject via the syringe.

In step (q) above, any suitable method of mixing known in the art may be used, such as, illustratively, by manual means or by using an electric mixer, and the like.

injectable, moldable, and self-healing when manipulated. Further, the BM compositions herein are capable of absorption of growth factors, bone marrow aspirates, and other agents without compromise of their wet field integrity. Wet field integrity, moldability, Injectability and stickiness (e.g., to surgical gloves) was evaluated. Wet field integrity is simply placing a quantity of material in PBS and assessing the breakdown behavior (Integrity) as a function of time. Injectability is assessed by the ability to express material from the 10 cc open bore syringe (product pre-loaded). Moldability is assessed from the ability to manipulate the material by hand without crumbling or falling apart and being able to reconstitute into the original mass shape (e.g. a ball or elongated roll). Stickiness is mostly qualitative assessment of the amount of material adhering to (sticking) surgical gloves during manipulation of the material. Wet field integrity may be quantified according to the following chart:

| 1 | 2 | 3 | 4 | 5 |
|---|---|---|---|---|
| Holds together 1-3 minutes in wet field environment | Holds together 3-5 minutes in wet field environment | Holds together 5-10 minutes in wet field environment | Holds together 10-20 minutes in wet field environment | Holds together >20 minutes in wet field environment |

Between steps (q) and (r) above, the contents of the glass mixing bowl may be transferred prior to cooling to another suitable container, such as, illustratively, a cartridge, and the like.

In step (r) above, any refrigerator temperature that results in gelling of the putty may be used.

In step (u) above, any suitable method of packaging under sterile conditions known in the art may be used herein.

Figure 32A:
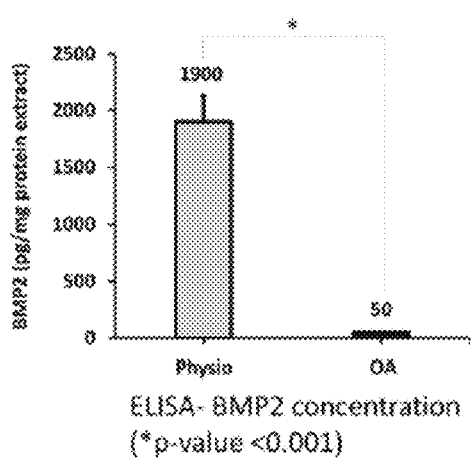
FIG. 32A,B are graphs showing BMP-2 content.
Figure 32B:
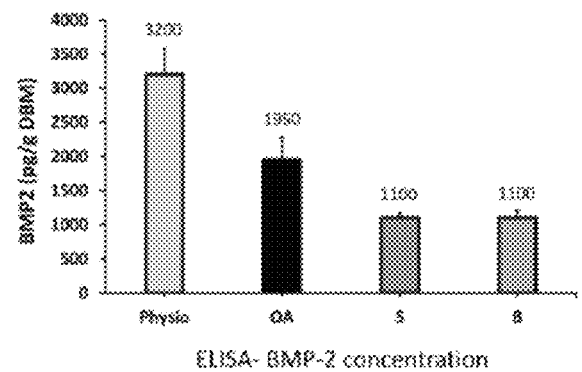

In another embodiment, the present disclosure describes novel DBM bone graft compositions that are produced by the methods described herein. These DBM compositions are 100% human (i.e., physiologic), and are fully compliant with the FDA's HCT/P regulations. Thus, the novel bone compositions are typically comprised fully of human demineralized bone matrix, and typically do not require the inclusion of additional materials such as carriers or delivery agents, nor do they require the inclusion of binders. Further, the DBM compositions are fully compliant with the standards of the American Association of Tissue Banks (AATB), especially as pertains to having residual $Ca^{+2} < 8\%$. It is nonetheless to be understood that, if desired, certain DBM products possessing residual $Ca^{+2} > 8\%$ may be intentionally made by the methods herein, and are contemplated as part of this invention. In one aspect, the DBM compositions herein include a physiologic compilation of growth factors that are related to osteoinductivity, osteoconductivity, and osteogenesis, including various bone morphogenetic proteins (e.g., BMP-2, BMP-4, BMP-7, VEGF, OCN, OPN, RUNX-2, RANK-L and the like); these bone morphogenetic proteins are included in highly bioavailable form (as shown in FIGS. 32A-B). The BM compositions herein have the characteristics of possessing a physiologic collagenous microenvironment and physiologic bioavailability of growth factors that are conducive for osteogenesis. Further, the DBM compositions herein exhibit pre-osteoid mimicry that is conducive for osteogenesis.

Figure 25:
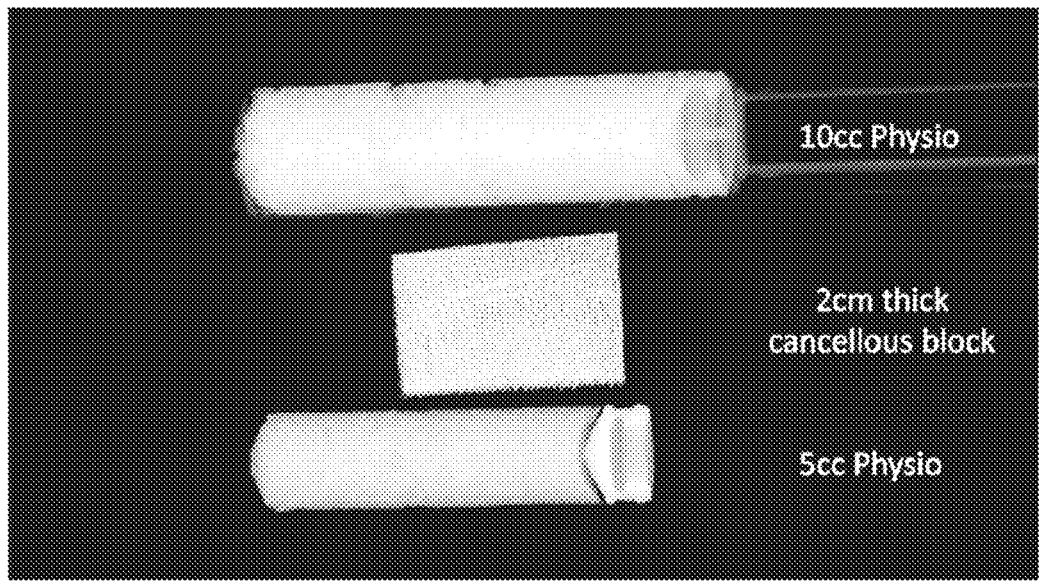
FIG. 25 displays the radiopacity of BM product according to one example of the disclosed invention.
Figure 26:
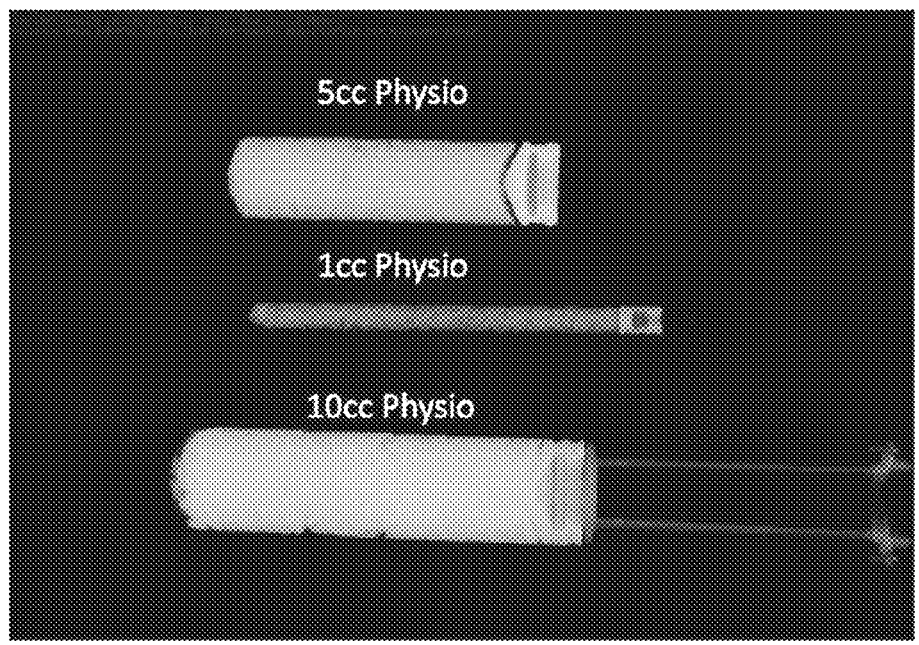
FIG. 26 displays the radiopacity of BM product according to another example of the disclosed invention.
Figure 27:
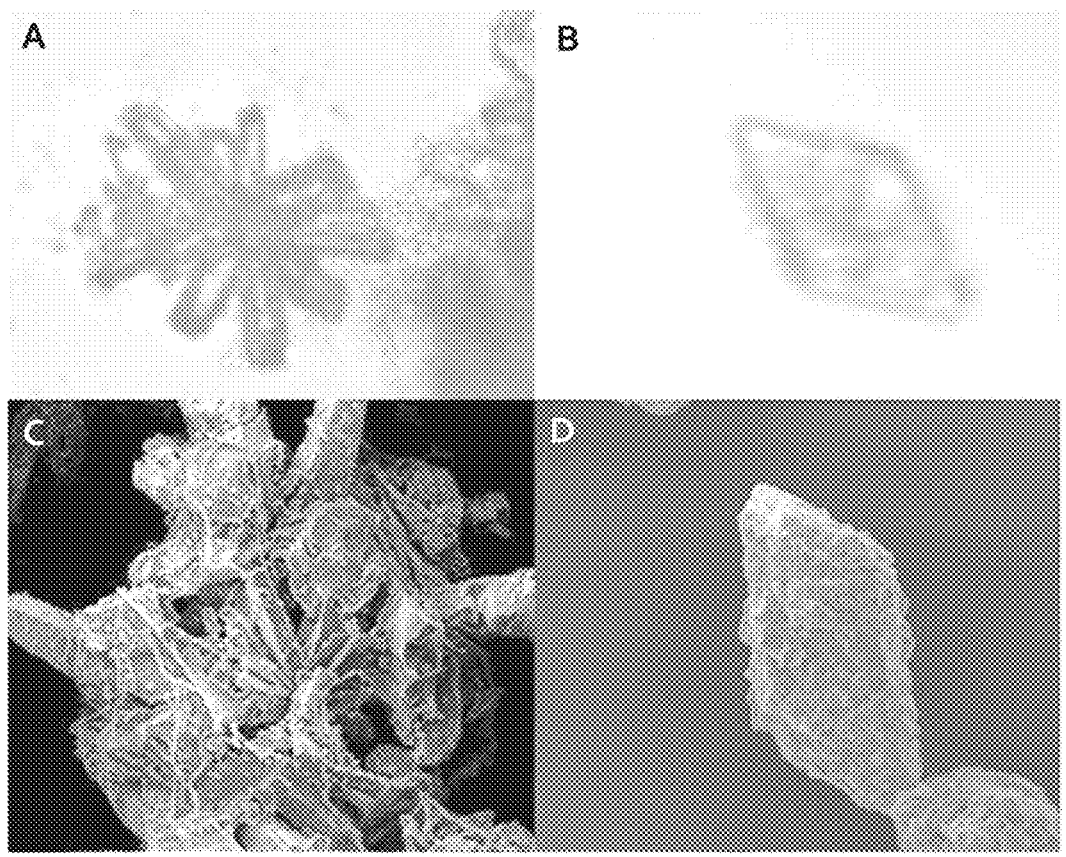
FIG. 27 shows brushite and monetite images from both optical and scanning electron microscopes.
Figure 28:
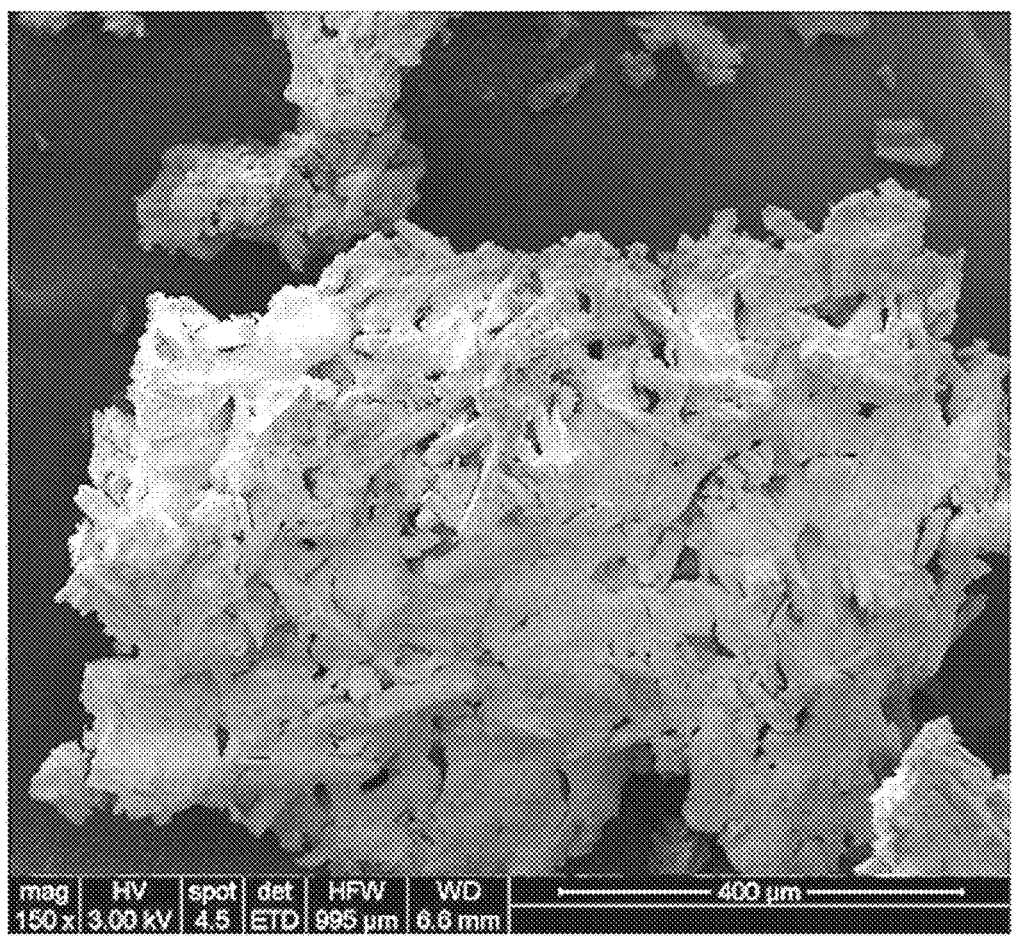
FIG. 28 shows a scanning electron microscope image of one example of a bone matrix according to the disclosed invention in a mixture of collagen, gelatin, and growth factors.
Figure 29:
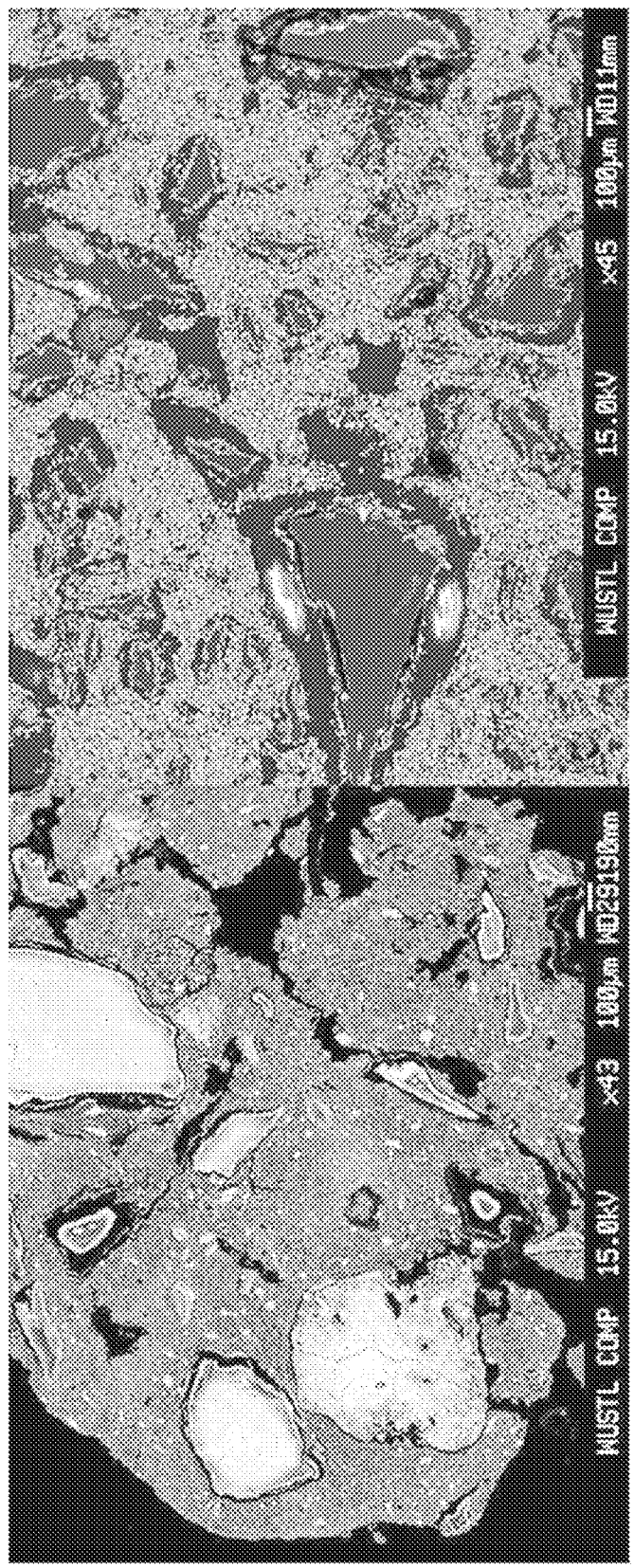
FIG. 29 shows backscattered scanning electron microscope images of one example of a bone matrix composition.
Figure 30:
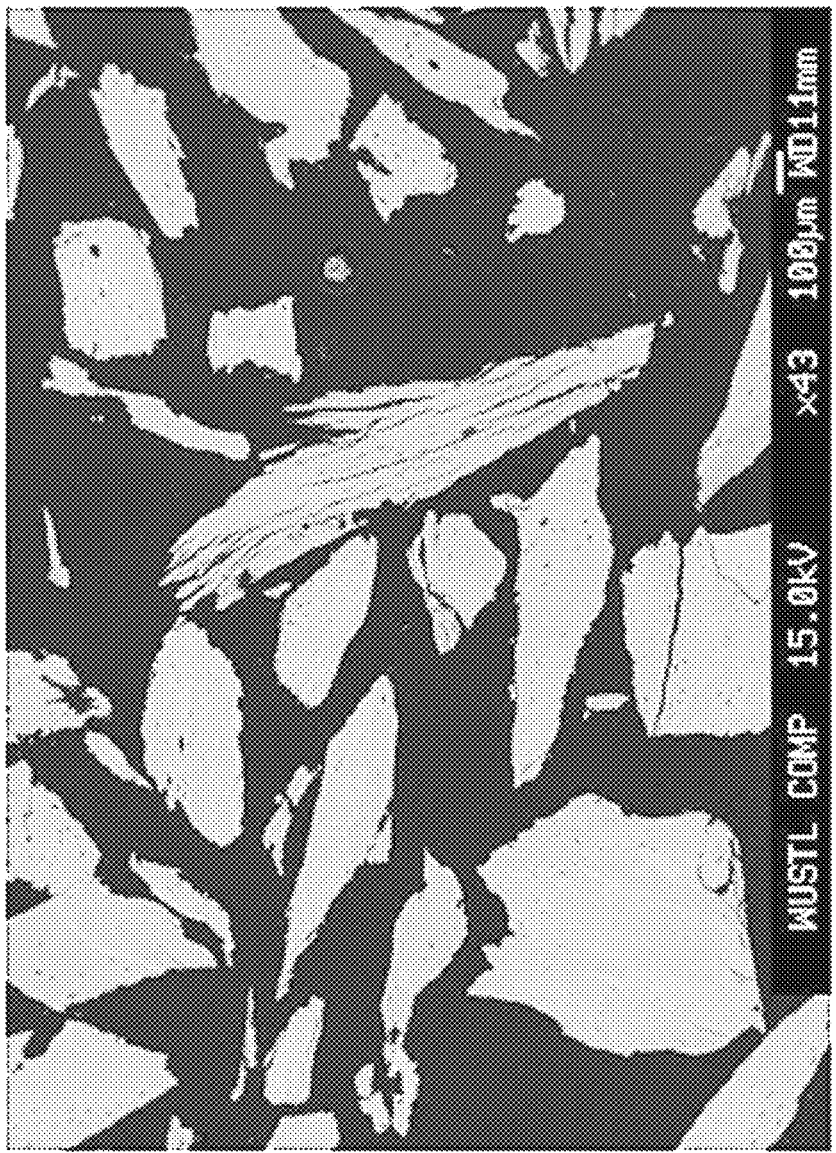
FIG. 30 is a backscattered scanning electron microscope image of another example of a bone matrix composition.
Figure 31:
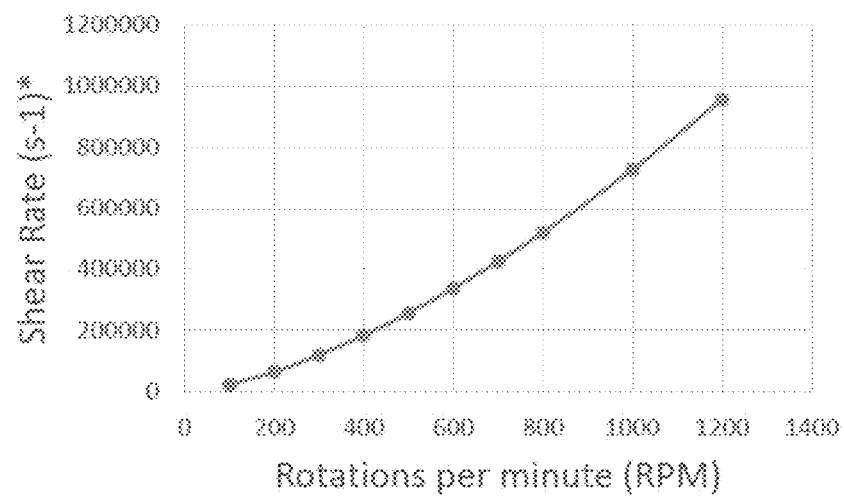
FIG. 31 is a graph showing RPM vs. Shear Rate.

Another characteristic of the BM compositions herein is that they possess high wet field integrity, and do not substantially wash out or deform in a wet environment, such as in a surgical environment. The BM compositions herein are In another embodiment, the BM graft products, prepared by the methods described herein, possess physiologic biomineralization characteristics as they retain calcium and phosphorus mineral salts in the form of Monetite ($CaHPO_4$) and Brushite ($CaHPO_4.2H_2O$), both of which have been reported to possess osteoconductive and osteoinductive properties, respectively, and also are known precursors to hydroxyapatite ($HA_p$) bone formation in situ. The formation of the Monetite and Brushite in these BM products was unexpected, and appears to result from crystallization of these compounds during the process steps. Images of Monetite and Brushite are shown in FIG. 27. An example of a BM product according to one embodiment of the disclosed invention is shown in FIG. 28. FIGS. 29-30 show examples of backscattered scanning electron microscope images representing a range of mineralization and demineralized components within the bone matrix compositions. The "bright" larger pieces seen in –014 represent a higher residual original bone particles/structure content compared to the "darker" larger particles seen in –025. Conversely, the surrounding 'mileau' has more "bright" CaP (M &B) in –025 compared to a lesser amount seen in –014. Without being bound by theory, it is believed herein that the elongated, needle-like crystals of these compounds may be partially responsible for the observed excellent wet field integrity of the products, presumably due to their ability to hold the matrix together. The exact ratio of Monetite to Brushite may vary, but typically the final bone product comprises approximately 16-80% Brushite and 16-50% Monetite, with the remainder of the mineral portion being hydroxyapatite. Typically the total mineral content in the final material is 46-74% by weight. The BM products herein also possess an excellent degree of radiopacity, thus lending themselves to good visualization and imaging. Examples of such radiopacity are shown in FIGS. 25-26.

The following table provides a partial summary of some of the features and embodiments of the BM products and BM production methods of the invention:

BM products are 100% human (physiologic)
BM products do not require the use of carriers, and are HCT/P compliant
DBM products have a residual [$Ca^{+2}$] <8%, i.e., AATB compliant or >8% [$Ca^{+2}$] for HCT/P compliance.
BM products comprise physiologic compilation of growth factors
BM products do not require the use of binders or poloxamers
BM products possess excellent wet field integrity, i.e., do not undergo wash-away in surgical field, do not irrigate or dissolve upon implantation, are easier to handle with less sticking to gloves and less waste
BM products are injectable, moldable, and self-healing when manipulated
BM products can be co-mingled with and undergo absorption of growth factors, bone marrow aspirate (BMA), and other agents without significant compromise in regard to wet field integrity
BM products undergo physiologic biomineralization, retaining calcium and phosphorus in the form of Monetite and Brushite, both of which are known precursors to HAp (bone) formation in situ
BM products possess excellent radiopacity, these lending themselves to good visualization and imaging
BM products provide a physiologic collagenous microenvironment for osteogenesis
BM products comprise physiologic, bioavailable growth factors for osteogenesis
BM products exhibit pre-osteoid (osteogenesis) mimicry
BM products exhibit predictable resorption properties (fractionated collagen)
BM products can be produced in various forms including clay, paste, crush, putty, gel or powder, thus offering surgeons a multiplicity of options, formed into sheets, sleeves, trays, boats for containing other bone grafts.
Method of production of BM products results in voluminization from starting bone stock, yielding 2-3 times quantity by weight
Method of production is a single batch process, leading to improved consistency, significantly shortened production times, and large output volumes
Method of production leads to BM products comprising BMP-2 in greater quantities than those found in OsteoAMP ®, Burst, and Sterifuse ™ commercial products
Method of production provides BM products that are cleaner, "whiter" and more esthetically pleasing than other available DBM products
Method of production provides consistent formulation in regard to touch, with no clumps or chunks
Method of production is highly reproducible, providing great consistency and reliability It is to be understood that, as contemplated herein, the BM products and the methods of their production disclosed herein may find utility in a variety of other applications besides those in the foregoing, such as, but not limited to the following: (1) In a multitude of implants where the implant/host juncture is compromised due to lack of bone, bone quality; (2) in applications where there is a need to possibly push through fenestrated screws or rods, and the like; (3) in cosmetic surgery, such as, illustratively, nasal, oral, and the like; (4) in situations where there is a need for bone lengthening in order to help expedite bridging, and the like. Oncology, trauma, ortho-reconstruction, craniomaxillofacial (CMF), dental, podiatry and spine all have clinical utility for such improved bone matrix constructs.

EXAMPLES

The following examples are provided for the purpose of illustration only, and it is to be understood that they are not intended to be limiting, but that other modifications that are known to those skilled in the art, and that are within the scope and spirit of the disclosure herein, may be used as well. The ground bone powder used herein is typically obtained from single donor long bones, both cortical and cancellous

Example 1

An illustrative preparation of a BM under CVDS conditions in accordance with one embodiment of the disclosed invention. The following is a list of the raw materials used in this illustrative example: ~420 g of ground bone powder (particle size <1 mm); ~4300 ml of 1N Hydrochloric Acid (HCl) (pre-warmed to 37° C.); 40 L of 10% Potassium Phosphate Buffer solution (K2K), pre-cooled to 4° C.; 2 L of Deionized Water, pre-cooled to 4° C.; 4 L of Acetone, pre-cooled to 4° C.; pH test strips; spray bottle filled with Acetone. The following is a list of additional glassware used: 12×2 L Pyrex beakers; 4× Pyrex drying trays; 1× Pyrex mixing bowl.

An Instatherm® 6 L reactor (e.g., from Ace Glass, Inc.) was used in this preparation. A typical apparatus set-up, including the reactor, mechanical stirrer, thermocouple, and other associated parts, is shown in FIG. 1. The set-up in FIG. 1, including all of its components, should be recognizable by those skilled in the art. The procedure was carried out under sterile conditions, following standard sterilization procedures known in the art. The procedure included the following:

Safety clothing and eye and face protection is worn, and it is ascertained that fume hood is turned ON.

Bottom Cap insertion: Clear plastic (PTFE) threaded piece is attached to the flat side of the white PTFE cap to facilitate draining from the bottom of the reactor. A valve with a spigot can then be inserted in the clear plastic piece. Insert glass and plastic filters (100 micron) in the bottom interior of the cap. Insert the beveled, white o-ring to secure filters. Insert the round red o-ring on the outer threads. Screw (only finger tight) cap onto vessel.

Lid attachment: (i) The 5 threaded inserts that can be coupled with the lid of the reactor; (ii) the middle insert is open on both sides and will be used to insert the stir shaft; (iii) screw in (only two-finger tight—NEVER overtighten) two capped ends with O-rings; (iv) screw in caps with vented connectors; (v) place small black O-ring on valve and insert into cap with hole, place large red O-ring in lid, and attach lid and secure metal clamp around Lid—Reactor joint.

Instatherm® 6 L reactor alignment: (i) Place level on bottom platform to insure it is parallel with the ground; (ii) place Instatherm® Reactor (6 L) with bottom cap face down on the platform with one of the glass windows aligned to offer visualization into the reactor from the front; (iii) use red chain clamp to secure reactor in place; (iv) secure reactor by securing and tightening the chain clamp; (v) insert stir shaft into reactor; (vi) place lid on top of the reactor with stir shaft through the middle opening insert in the lid; (vii) place lid on reactor and make sure seal is formed with the large (red) O-ring; (viii) attach metal retaining clamp to secure lid to reactor; (ix) place level on lid and make sure lid is parallel to the platform; (x) position stirrer motor above the reactor and use the level to make sure that it is parallel to reactor and platform; (xi) insert stir shaft into adjustable chuck on stirrer motor; mark on the teflon where the stir shaft is flush with the bottom of the reactor; lift up, past mark by ~2-4 mm to assure that the stir shaft is not sitting on the bottom of the reactor; (xii) lock stir shaft into the stirrer motor with chuck key; (xiii) manually spin stir shaft to feel and visualize any obstructions and to assure alignment; (xiv) turn on stirrer motor with range first set to second level (NB: do not exceed ~400 RPM without liquid when assessing stir shaft alignment); (xv) make adjustments by moving the bottom of the reactor until stir shaft rotates as freely as possible; stir shaft should rotate smoothly (visualize with flashlight through window and touch top of Teflon stir shaft).

Thermocouple placement: (i) Insert thermocouple into black plastic coupling, with upper and lower O-rings in place; (ii) insert thermocouple into reactor; secure into place with 2 O-rings on either side of the coupling. (NB: the bottom of the thermocouple should reside midway into the expected liquid level); (iii) insert two pronged end into female end (J-Kem System); (iv) turn on J-Kem Thermocouple.

Introduction of 1N HCl: The 1N HCl is added to reactor as follows: (i) unscrew one of the solid caps on the reactor lid; (ii) insert plastic funnel into reactor lid; (iii) slowly pour 4 L warmed (37° C.) 1N HCl acid into reactor; (iv) turn on J-Kem heating system (pre-set to 55° C.) initially using the 300 ml-2 L (60V) setting and after ~15 minutes, adjust to full power setting; make sure power cord is attached correctly (insert and rotate until receptor clicks) to the Instatherm® cord on reactor, as well as assuring the thermocouple is attached to J-Kem system; set the stir shaft to ~400 rpm.

Addition of Bone Powder: Add bone powder to reactor when temperature of acid in reactor has reached 55° C.; (i) unscrew one of the solid caps on the reactor lid; (ii) insert dry glass funnel (58° offset) into vessel lid; (iii) turn stir shaft up to >600 rpm; (iv) slowly pour (tap) the 420 g of bone powder into the reactor and stop when foam is visible (adding too much too quickly can cause excessive foaming); best practice is to add ~½ (half) of the powder initially, then add the remainder after the foaming is controlled (<~10 min. total time); use a short segment of PTFE tubing to gently clear funnel if it becomes plugged with powder; (v) turn stir shaft up to 800 to 1000 rpm; (vi) continue pouring bone powder until all of the powder has been added; (vii) use an additional ~300-500 ml of warmed 1N HCl to rinse any residual bone powder into the reactor; (viii) mix at a rate of at least ~800 up to 1000 rpm at 55° C. for 1 hour.

Acid Arresting Reaction (1 hour after bone is added): (a) Turn off Instatherm® heating power; (b) turn stir shaft to ~400 rpm; (c) add pre-chilled Potassium Phosphate Buffer Solution (K2K Solution) to reactor: connect tubing from buffer carboy to valve on top of the reactor lid; run tubing through Peristaltic pump and connect to $K_2K$ carboy valve; insert tubing with ferrules inserted to seal in place; unscrew top cap on $K_2K$ carboy to assure airflow for dispensing; make sure pump is set to flow into the reactor; pump $K_2K$ buffer solution into reactor until solution level reaches the reactor-lid junction; turn off stir shaft and allow powder to settle inside reactor; check pH with indicator strip (goal is a pH>6).

Repeated Acid Arrest: (a) Decant (or suction) supernatant into 2000 ml (2 L) beakers: (i) Decant (or suction) ~200-400 ml of supernatant to each of the 12 beakers; (ii) add buffer solution to each beaker until pH>6 (check pH with indicator strips); (iii) replace decanted supernatant with chilled K2K buffer solution in the reactor; (iv) repeat until pH is >6. (b) Wash away possible salt precipitate: (i) Decant (or suction) solution into a large waste container (be careful not to remove any powder or visible proteins); (ii) add deionized water, $H_2O$ (or distilled water) to dissolve any salts that may have formed when the buffer was added to acid; (iii) decant water/salt solution into waste container. (c) Final Preparation: (i) Pour acetone over precipitates in each beaker and the vessel; (ii) allow precipitate to settle for a minimum of ~1 hour or overnight (if necessary); (iii) decant (or suction) as much of the excess acetone as possible.

Protein Extraction: (a) Remove acetone from beakers: (i) Decant (or suction) acetone from beakers into a waste container (some beakers may have floating proteins; gently tap the beakers on the table to remove any trapped air bubbles); (ii) pour contents of each beaker and vessel into the Pyrex drying trays; separate each drying tray as indicated by color: "white" fluffy appearance in solution, fluid liquid, "cream" viscous semi-solid paste, and tan "pulp"-like powder; (iii) let residual acetone evaporate (this process can be accelerated by heating the acetone via use of a hotplate; do not exceed 55° C. as protein denaturing may occur). (Alternatively, a forced convection oven may be used to dry the pastes slowly, avoiding over drying into a powder).

Figure 2:
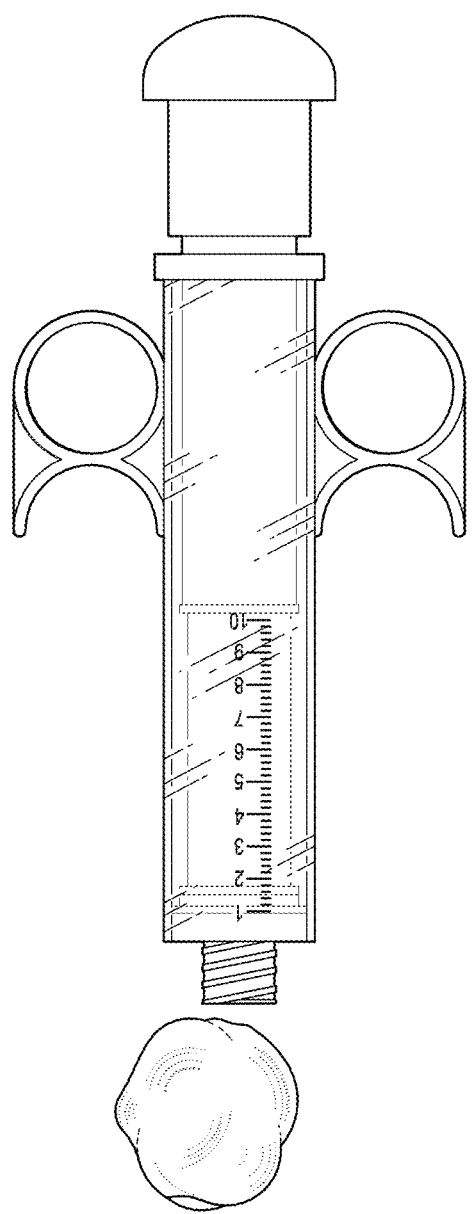
FIG. 2 displays a representative example of a DBM product prepared as described herein, being injected via a syringe.

Putty formation: Once acetone is evaporated, combine contents in a pyrex mixing bowl; mix until contents appear to be homogenously combined; allow mixture to congeal in refrigerator at 4° C. until the desired rheology is achieved. Possible storage additives may be added at this point to assure shelf-life. FIG. 2 shows the putty being injected via a 1 mL, a 5 mL, and a 10 mL syringe.

Example 2

A Second Illustrative Preparation of a DBM under CVDS Conditions in Accordance with the Invention. The following is a list of the raw materials used in this illustrative example: 289.7 g of ground bone powder (particle size 1 mm); ~4200 ml of 1N HCl; 12 L of 0.5M Potassium Phosphate Buffer solution (K2K).

The procedure was carried out under sterile conditions, including the following. The demineralization apparatus was set up in a manner similar to the preceding example. The stirrer was turned on and run at 400 rpm, and the 4 L of 1N HCl was added slowly with heating. After all of the HCl was in the vessel, the stirring rate was increased to 600 rpm, and heating was continued up to a temperature of ~55° C. The lid plugs were removed, the stirring rate was increased to 800 rpm, then to 1000 rpm, and the bone powder was added slowly via a funnel during about 6 minutes, rinsing the last portion of bone powder with 250 mL of 1N HCl pre-warmed to 37° C. After about 1.5 h, heating and stirring were stopped, and the vessel contents were poured into a sterile bucket. The 0.5M Potassium Phosphate Buffer solution ($K_2K$) was added slowly with gentle stirring, until a pH of around 6 was achieved, as determined by using indicator strips.

Separation of the BM was accomplished by using centrifugation. The buffered contents of the sterile bucket were poured into centrifuge bottles, and centrifugation was carried out in multiple batches as needed (optionally, prior to centrifugation, a portion of the buffered contents of the sterile bucket may be poured into another sterile bucket, if needed, for later centrifugation). The centrifugation step may be carried out at exceedingly high centrifuge spinning speeds, such as, illustratively, up to 4200 rpm. Also, the centrifugation step may be carried out under reduced temperatures, even down to as low as −5° C. After centrifugation, the supernatant layers in the centrifuge bottles were decanted. The residues were rinsed with sterile water, and the rinsing water was decanted. Chilled acetone was added to each bottle. The quantity of chilled acetone may be one that is enough to cover the residual pellets or to fill each bottle all the way up to the nape, as needed. The bottles were stoppered and shaken vigorously, then the contents were poured into 5 Pyrex drying trays, rinsing the bottles with additional chilled acetone to dislodge adherent material. The drying trays were placed in a fan-assisted convection oven (commonly known as "FC oven") pre-warmed to 30° C., with the fan speed and damper pre-set at around 25% of maximum. After about 13 h, the temperature was raised to 39° C., and the fan speed and damper setting were increased to 100%. After about 2 h, moisture analysis on a sample showed 69.4%, and an injectability test on a sample in a 10 cc syringe showed the material to pass the test. At this point, all of the DBM material was transferred to a mixer bowl and mixed to homogeneity. Then the DBM material was transferred to a cartridge, and the cartridge was placed in a refrigerator to allow the DBM material to gel.

In another embodiment, described herein is a DBM bone graft kit. This kit comprises one or more syringes pre-filled with the DBM material prepared by the methods described in the foregoing. The kit also comprises packaging to encase the one or more pre-filled syringes. The packaging may optionally, but typically, be sterile, depending on the intended use. Illustratively, in order to prepare the kit that comprises the one or more pre-filled syringes in packaging, the cartridge in the preceding paragraph was allowed to thaw outside of the refrigerator, and the contents were dispensed into one or more sterile syringes, using any of the techniques common to those skilled in the art, thus filling the one or more syringes to the desired volume. The one or more filled syringes were double-bagged in sterile sealable bags (e.g., Nalgene), the bags were sealed, and then were placed in a freezer, allowing the syringe contents to gel again. The syringes were stored in the packaging as such, until ready for use or shipping.

Example 3

In this illustrative example, a DBM procedure is carried out in a manner similar to that described in Example 1 above, using 1N HCl, arresting with 50% phosphate buffer, rinsing sequentially with deionized water and acetone, and allowing the layers to separate into a bottom "Pulp" layer, a middle "Cream" layer, and an upper "White" layer, as depicted in FIG. 3. The layers are isolated and dried. As depicted in FIG. 3, if bone powder having particle size distribution (PSD) of 1-2 mm is used, DBM components (i.e., dried layers) are obtained that are in the form of a powder, a "crush" or a clay. The clay or crush have mineralized particles with a gritty "honeycomb" feel. If bone powder having PSD of <1 mm (e.g., 200-800 microns) is used, then DBM components are obtained that are in the form of a powder, a putty, and a gel (see FIG. 3). It is noteworthy that all of the components contain relatively high concentrations of various BMPs, as described later below and as evidenced in the data included in the attached addendum.

In one embodiment of the invention herein, a broad variety of DBM products are obtained by mixing together the different components described in the preceding paragraph in varying proportions, to provide DBM products exhibiting the desired rheology depending on the particular intended applications.

Figures 4A, 4B, 4C:
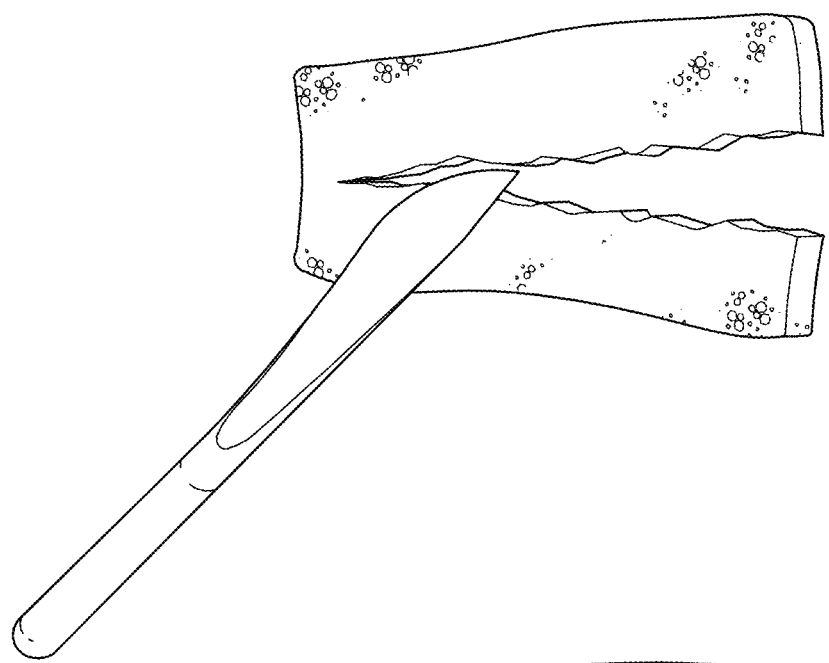
FIG. 4A, 4B, 4C show a BM product produced by the methods herein that is easily injectable, moldable, cuttable into strips, and formable into various shapes as needed.
Figure 5A:
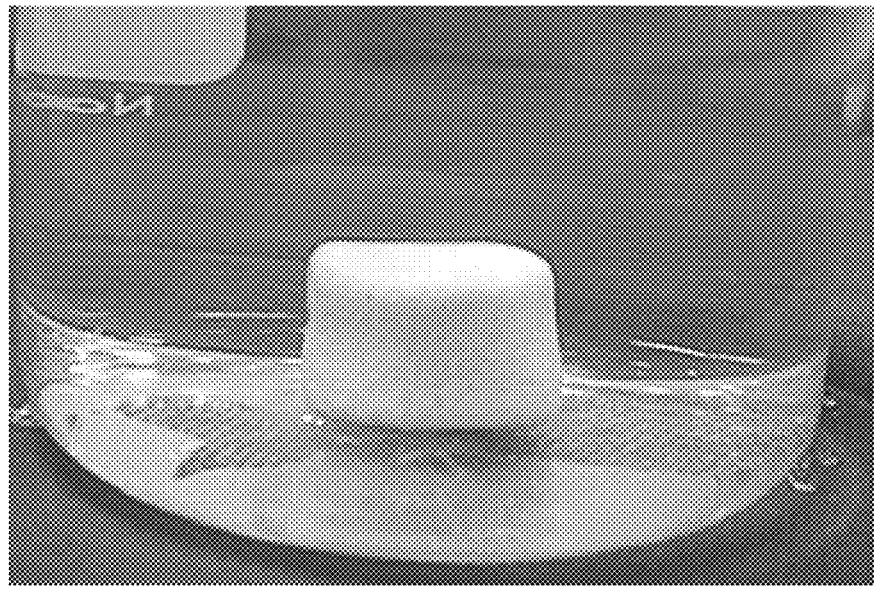
FIG. 5A shows a BM product produced by the methods herein.
Figure 5B:
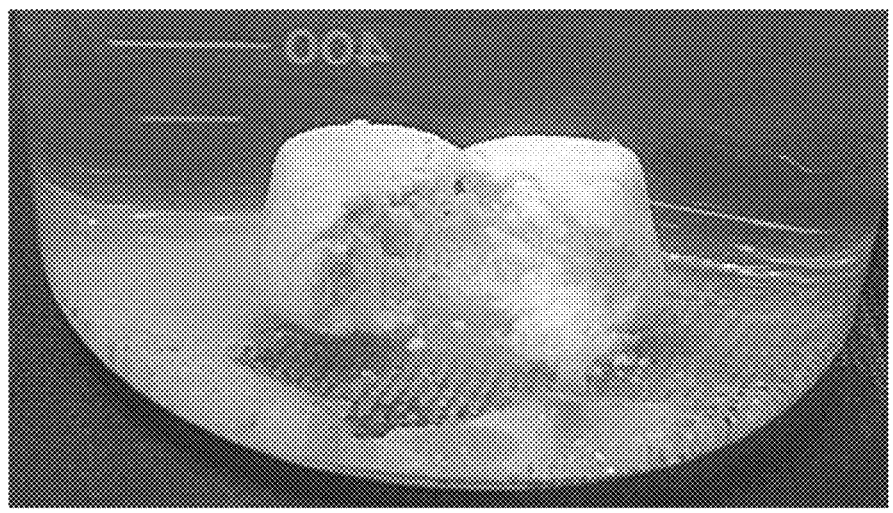
FIG. 5B shows the BM product produced by the methods herein that exhibits wet field integrity over time.

In FIG. 4A-C and FIG. 5A-B are shown representative DBM runs wherein the layers are undergoing mixing. A DBM powder produced by the methods herein and its ability to be molded back into a putty that is self-binding. FIG. 4A-C shows a DBM product produced by the methods herein that is easily injectable, moldable, cuttable into strips, and formable into various shapes as needed. FIG. 5A-B shows a DBM product produced by the methods herein that exhibits excellent wet field integrity. The product was immersed in water for several hours, then broken apart in the water, then removed and remolded into a lump that held itself together very well.

Example 4

FIG. 6 is a summary tabular display for all the materials/independent variables controlled during the demineralization process.

Example 5

FIG. 7 is a tabular display of CVDS characterization of all of the various DBM putties and clays. The mineral content was calculated through thermogravimetric analysis. The crystal percentages were all measured using X-ray diffraction analysis. The residual calcium percentages were measured using inductively coupled plasma-mass spectroscopy. Injectability was assessed by testing if the material could be expelled from a 10 cc syringe. NM stands for not measured. The red font represents an undesirable outcome.

Example 6

FIG. 8 is a tabular display of CVDS characterization of all of the various DBM gels. The mineral content was calculated through thermogravimetric analysis. The crystal percentages were all measured using x-ray diffraction analysis. The residual calcium percentages were measured using inductively coupled plasma-mass spectroscopy. Injectability was assessed by testing if the material could be expelled from a 10 cc syringe. NM stands for not measured. The red font represents an undesirable outcome.

Example 7

FIG. 9 is a tabular display of CVDS characterization of all of the various DBM powders. The mineral content was calculated through thermogravimetric analysis. The crystal percentages were all measured using x-ray diffraction analysis. The residual calcium percentages were measured using inductively coupled plasma-mass spectroscopy. Injectability was assessed by testing if the material could be expelled from a 10 cc syringe. NM stands for not measured.

Example 8

FIG. 10 is a tabular display showing a comparison of the mineral percentages calculated from x-ray diffraction analysis for the constituents of the two DBM samples R8 and R9. The demineralization time for R9 was 1.4 times that of R8. R8 Pulp can be seen to have a higher percentage of hydroxyapatite than the R9 Pulp.

Example 9

FIG. 11 is a tabular display showing a comparison of the mineral percentages calculated from x-ray diffraction analysis for all DBM materials. Specifically, the ratio of brushite to monetite is observed to assess its effect on injectability.

Example 10

FIG. 12 is a tabular data display for various DBM products. The data includes mineral content measured by thermogravimetric analysis, crystal percentages measured by x-ray diffraction, injectability tested with a 10 cc syringe, residual moisture range measured with a residual moisture analyzer, and various parameters of the DBM process. These parameters include gelation time (the time that the material is allowed to remain in refrigeration before injection) and the drying method used. nm stands for not measured.

Example 11

FIG. 13 is a tabulation of the results of the residual calcium analysis measured by ICP-MS. The samples were run in triplicate, so each run represents a single measurement. The final residual calcium was calculated by an average of all 3 measurements. It can be noted that all of the residual calcium percentages are less than 8%.

Example 12

A DBM putty was first dried in a forced convection oven at 39° C. for 48 hours. 10 ml of deionized water was added to the dry powder while mixing in a kitchen stand mixer. The results show that the powder could be reconstituted to a state that was both moldable and injectable through a 10 cc syringe.

Example 13

This particular example is an R9 mixing experiment designed to assess rheology of the R9 putty at different formulations. Separate constituents of the R9 putty (White, Cream, and Pulp) were mixed in different ratios by weight to create a unique formulation. After mixing all formulations, all of the samples were moldable and injectable through a 10 cc syringe. It was noted that the rheology of mixture 2 felt most similar to the R9 putty that was created in the original demineralization process.

Example 14

Figure 14:
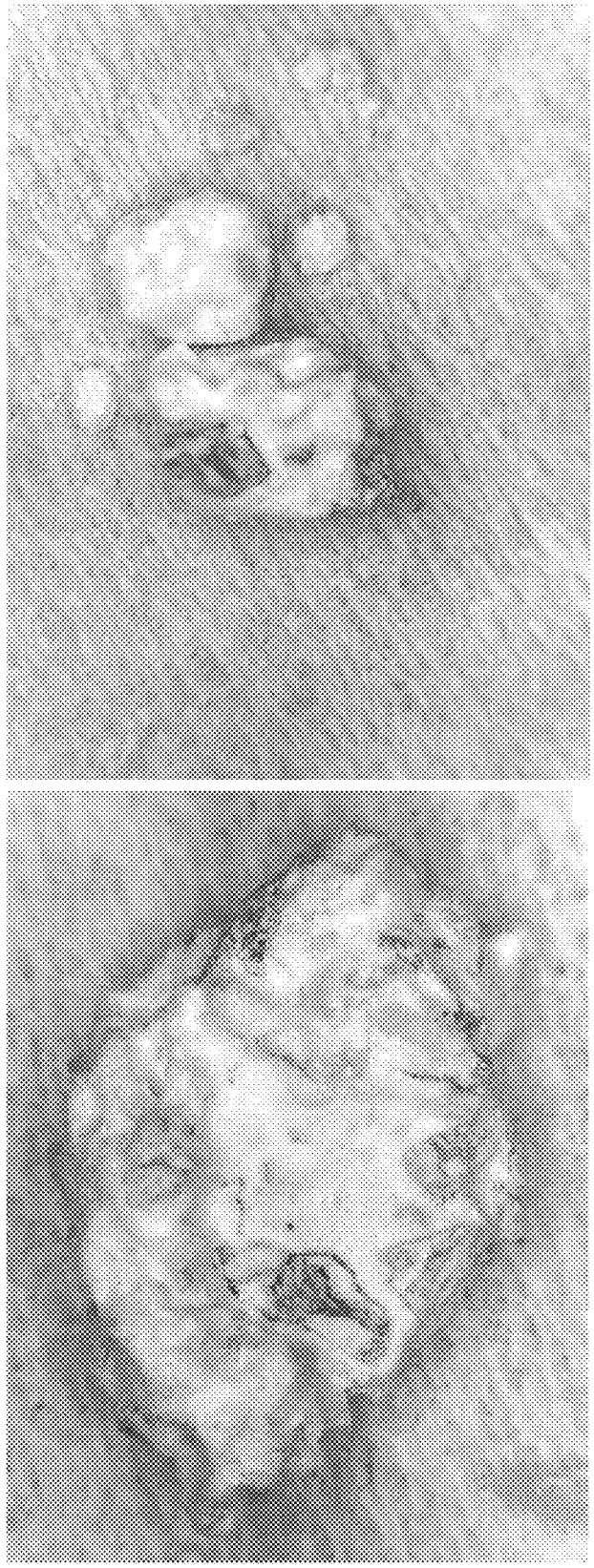
FIG. 14 displays digital reflected light microscopy images taken of a R10-V1 Putty particle.

FIG. 14 displays digital reflected light microscopy images taken of a R10-V1 Putty particle. It can be noted that beige colored particles are seen intermixed in the clump of dried R10-V1 Putty.

Example 15

Figure 15:
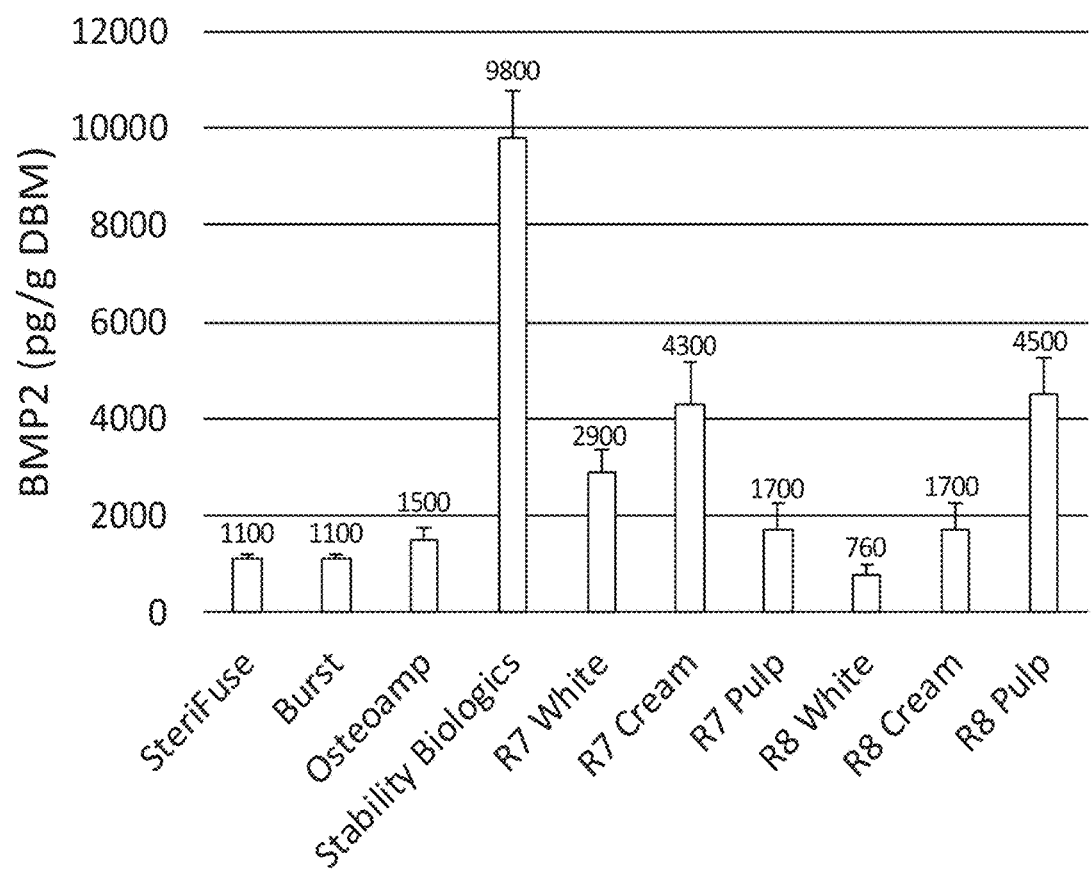
FIG. 15 shows BMP-2 measurements of various DBMs obtained using ELISA.

FIG. 15 shows BMP-2 measurements of various DBMs obtained using ELISA. The sample labeled "Stability Biologics" and those labeled R7 White, R7 Cream, R7 Pulp, R8 White, R8 Cream, and R8 Pulp are all DBM products or components of DBM runs of the instant invention. Most of the samples of the invention herein show higher BMP-2 content relative to the three commercial products Sterifuse, Burst, and OsteoAmp.

Example 16

Figure 16:
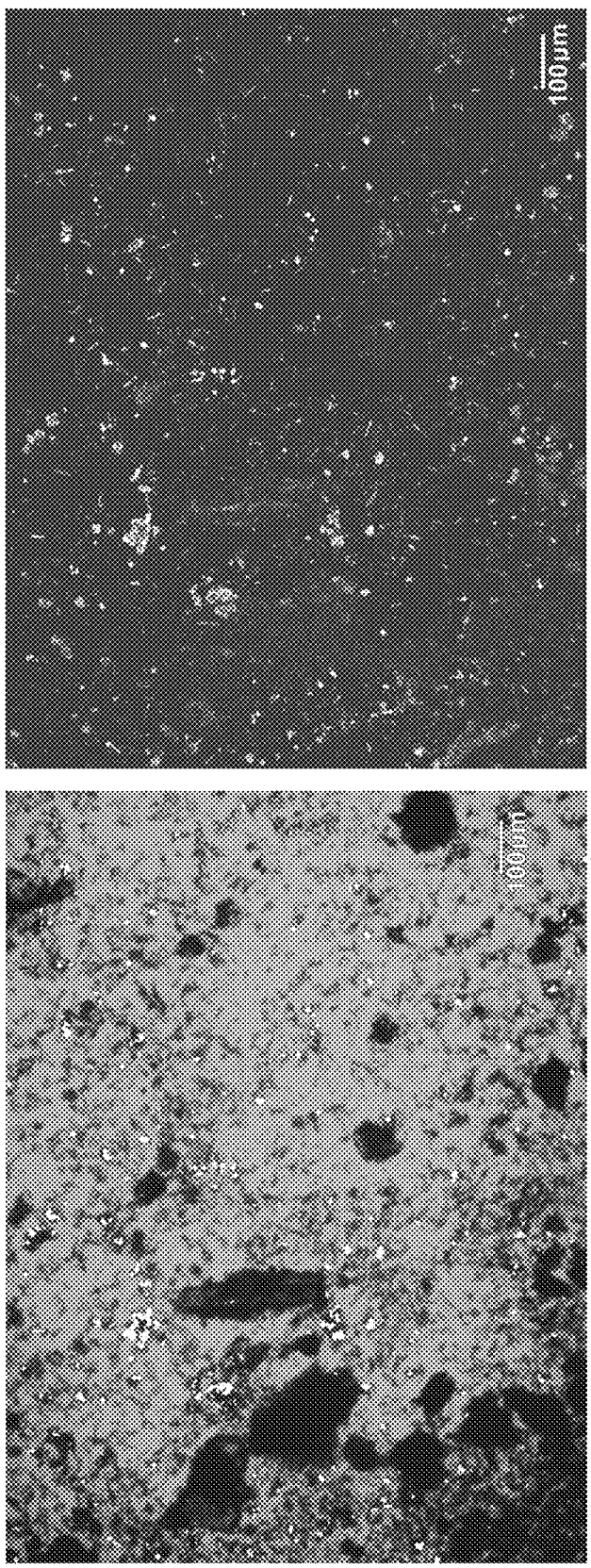
FIG. 16 displays 4× magnification birefringence images of V1 All-in-one.

FIG. 16 displays 4× magnification birefringence images of V1 All-in-one. The right image was taken with an optical microscope coupled with a linear polarizer. The right image was converted to a binary mask and overlaid over a brightfield image of the same location.

Example 17

Figure 17:
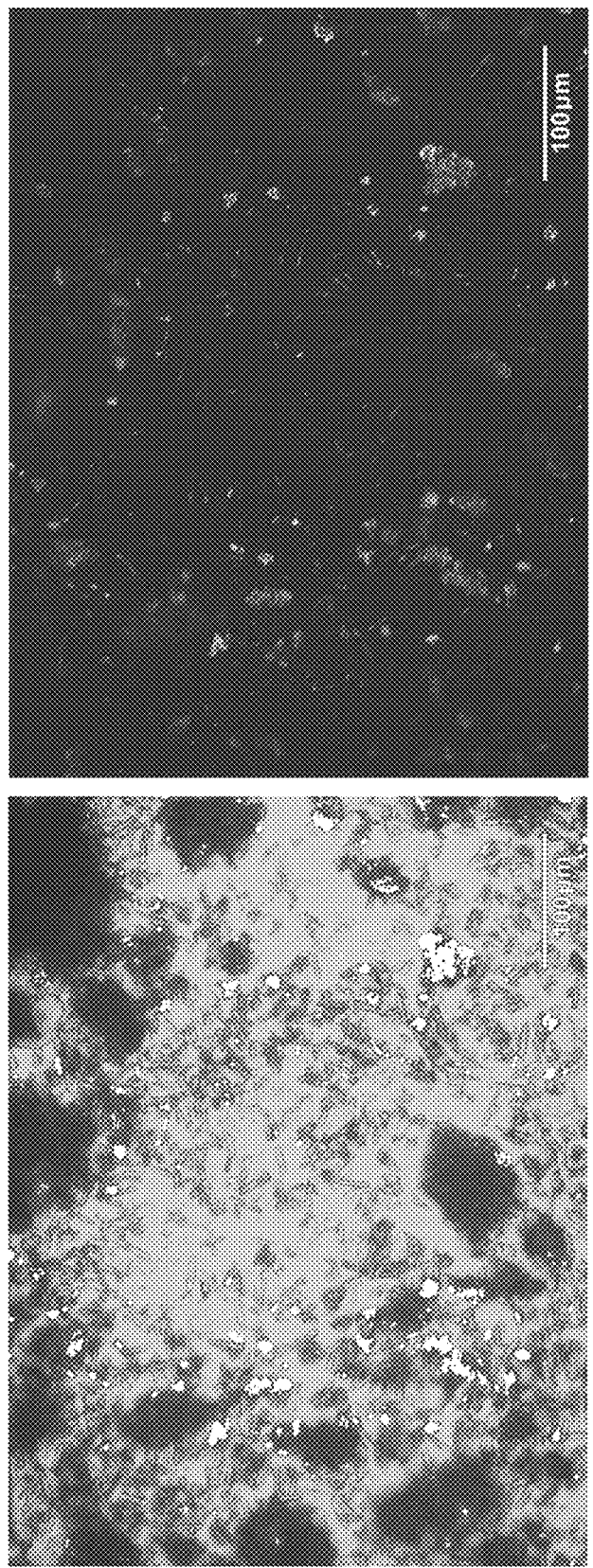
FIG. 17 displays 10× magnification birefringence images of V1 All-in-one.

FIG. 17 displays 10× magnification birefringence images of V1 All-in-one. The right image was taken with an optical microscope coupled with a linear polarizer. The right image was converted to a binary mask and overlaid over a brightfield image of the same location.

Example 18

Figure 18:
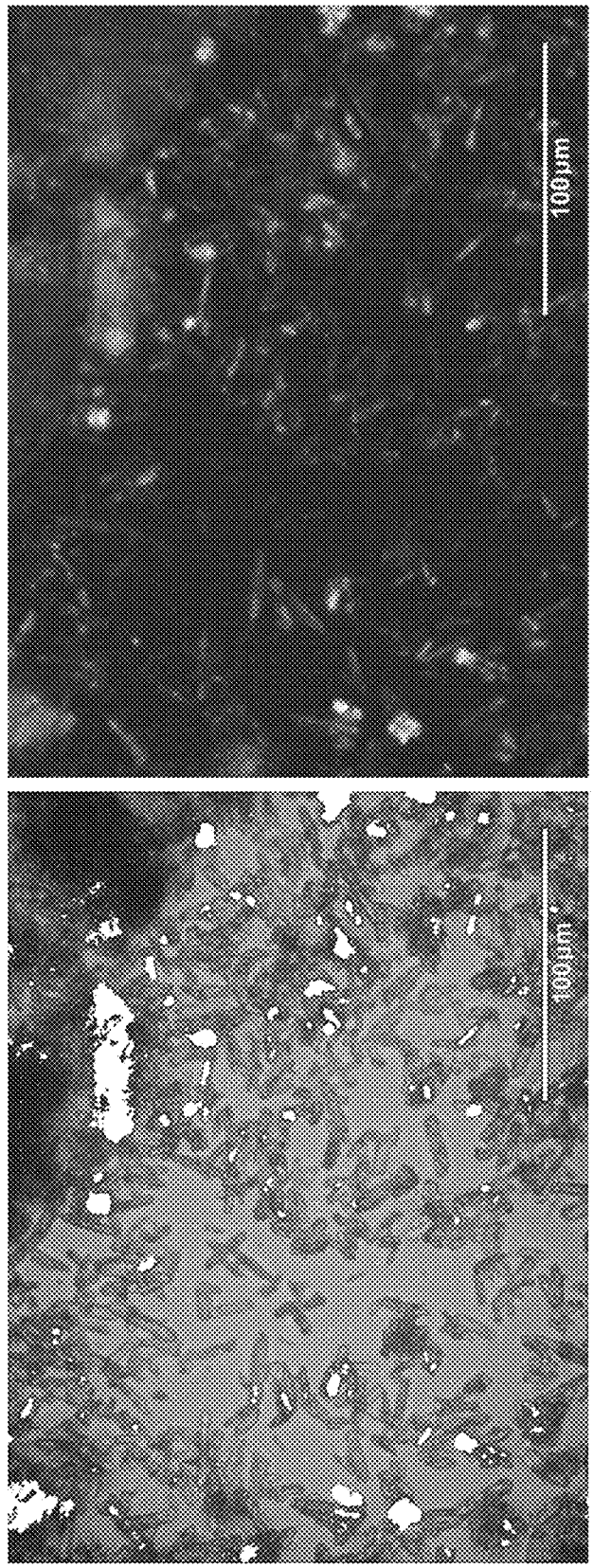
FIG. 18 displays 20× magnification birefringence images of V1 All-in-one.

FIG. 18 displays 20× magnification birefringence images of V1 All-in-one. The right image was taken with an optical microscope coupled with a linear polarizer. The right image was converted to a binary mask and overlaid over a brightfield image of the same location.

Example 19

Figure 19:
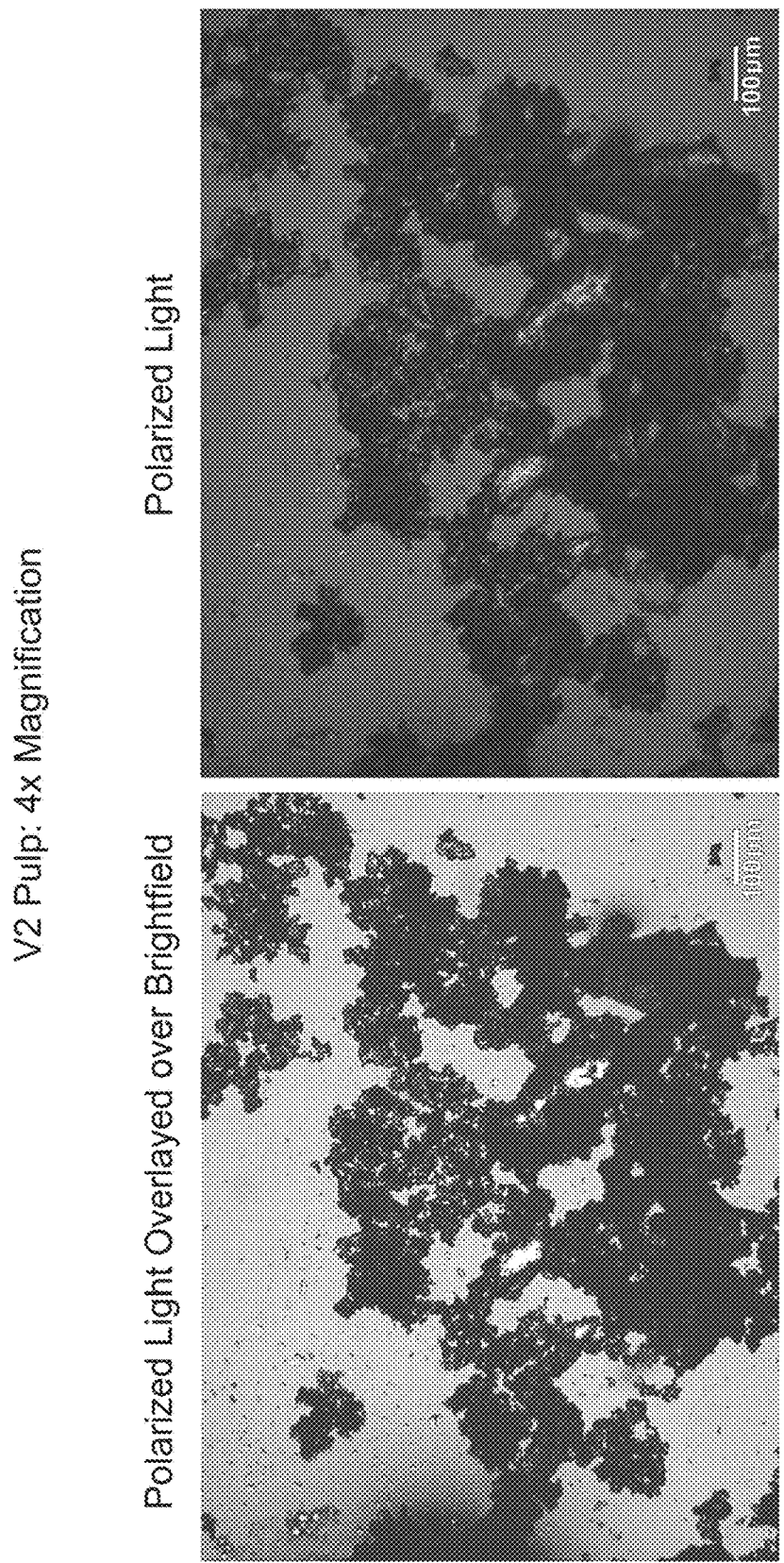
FIG. 19 displays 4× magnification birefringence images of V2 Pulp.

FIG. 19 displays 4× magnification birefringence images of V2 Pulp. The right image was taken with an optical microscope coupled with a linear polarizer. The right image was converted to a binary mask and overlaid over a brightfield image of the same location.

Example 20

Figure 20:
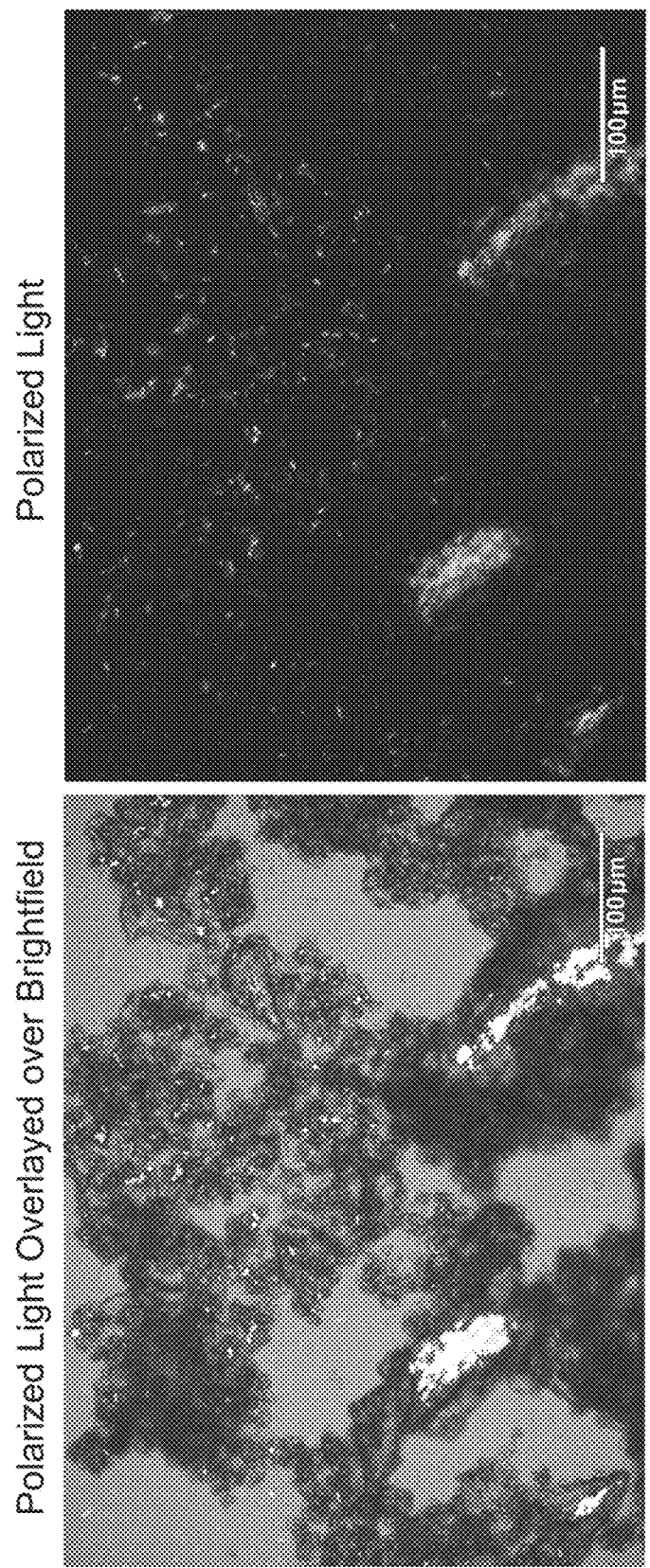
FIG. 20 displays 10× magnification birefringence images of V2 Pulp.

FIG. 20 displays 10× magnification birefringence images of V2 Pulp. The right image was taken with an optical microscope coupled with a linear polarizer. The right image was converted to a binary mask and overlaid over a brightfield image of the same location.

Example 21

Figure 21:
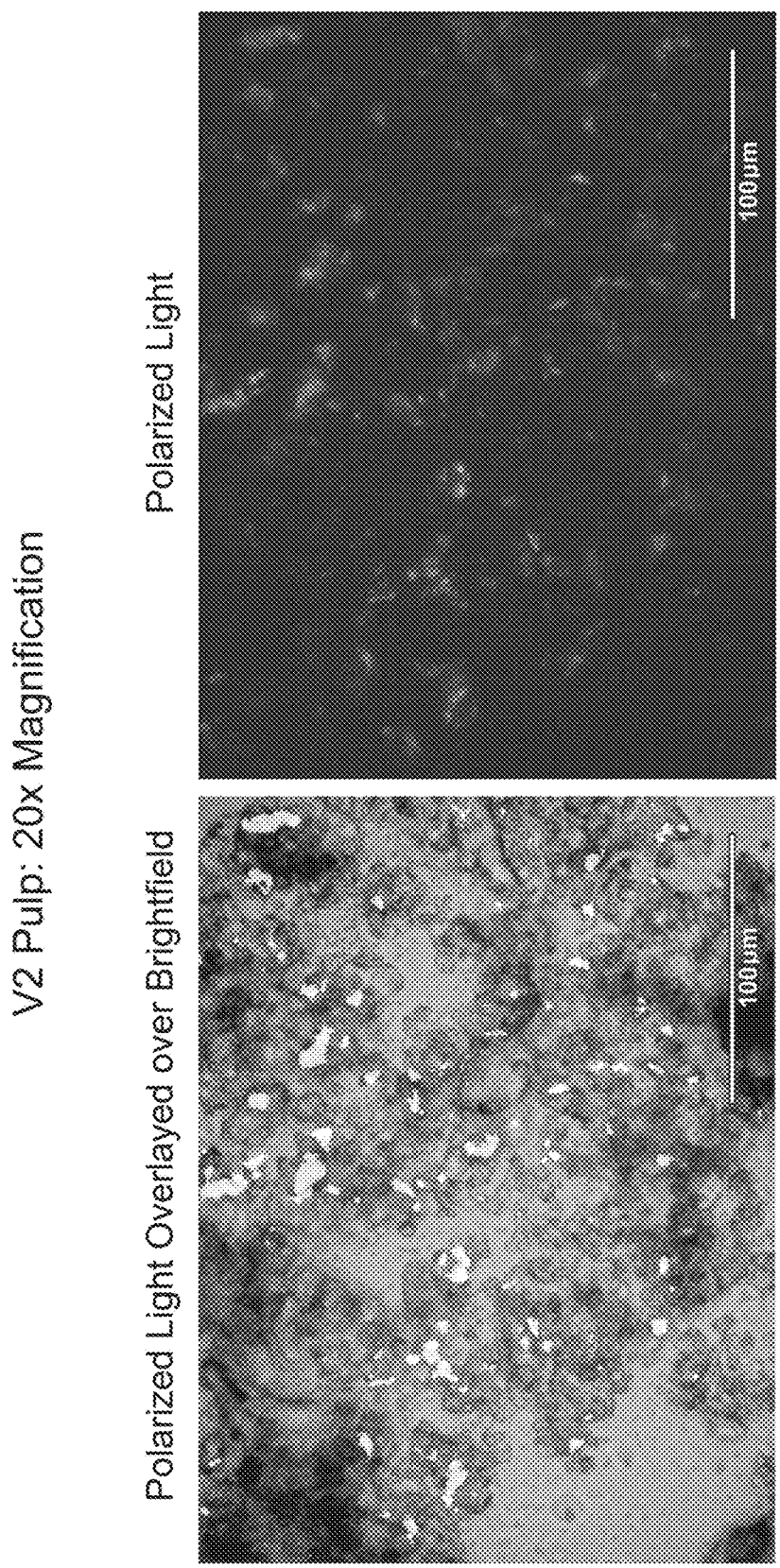
FIG. 21 displays 20× magnification birefringence images of V2 Pulp.

FIG. 21 displays 20× magnification birefringence images of V2 Pulp. The right image was taken with an optical microscope coupled with a linear polarizer. The right image was converted to a binary mask and overlaid over a brightfield image of the same location.

Example 22

Figure 22:
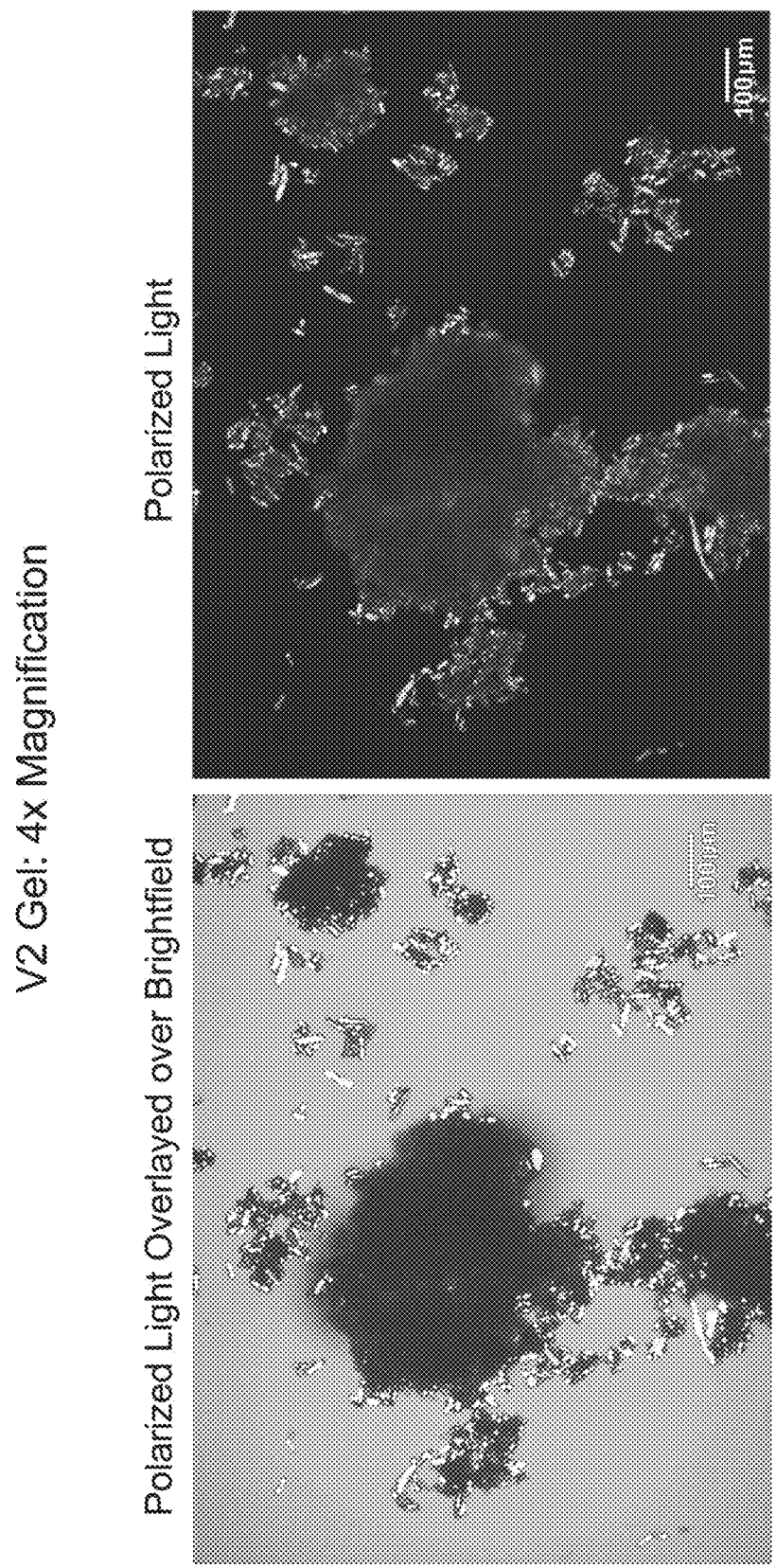
FIG. 22 displays 4× magnification birefringence images of V2 Gel.

FIG. 22 displays 4× magnification birefringence images of V2 Gel. The right image was taken with an optical microscope coupled with a linear polarizer. The right image was converted to a binary mask and overlaid over a brightfield image of the same location. The green areas represent particles with birefringence properties. It can be noted that rod-shaped particles surrounding the large dark particle appear to have birefringence properties.

Example 23

Figure 23:
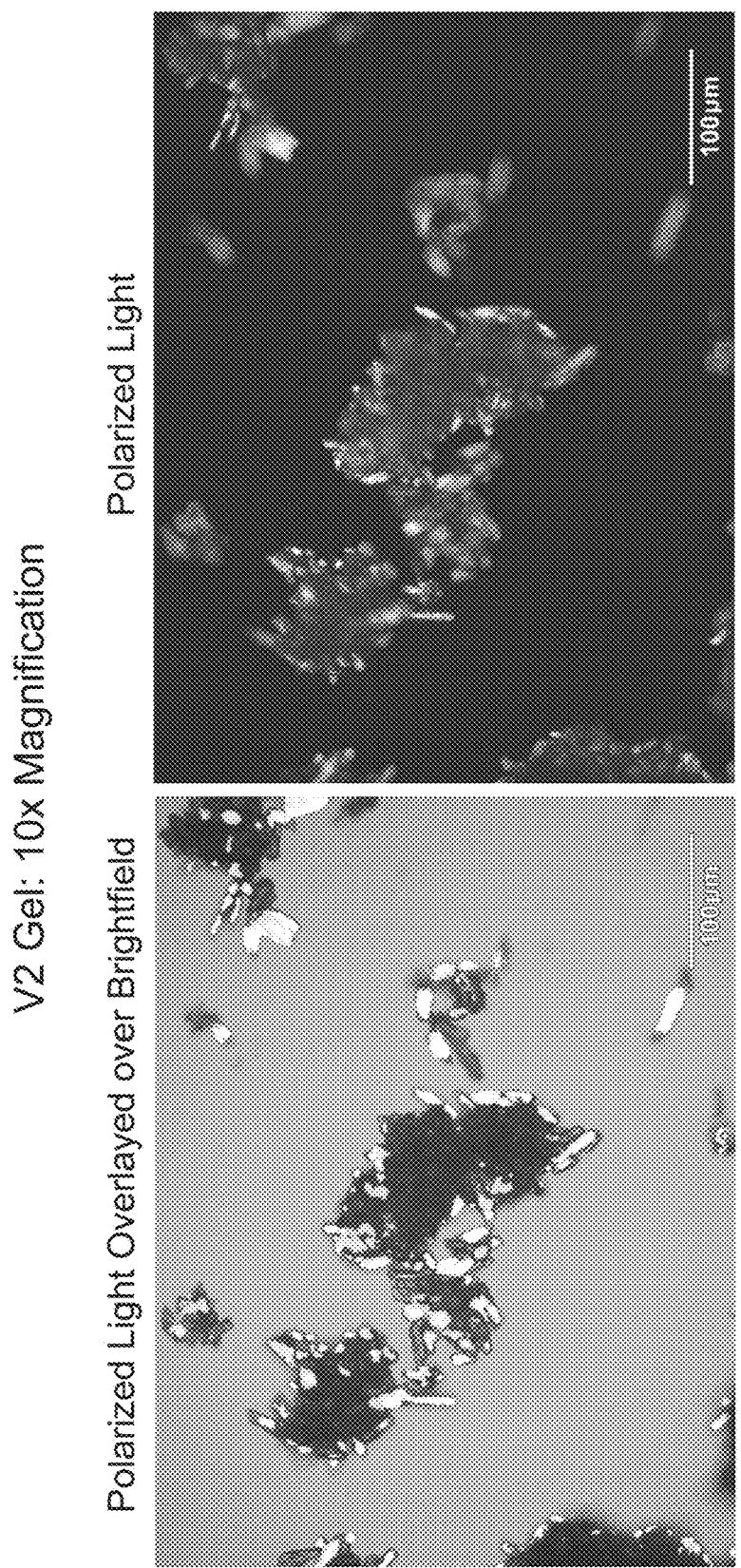
FIG. 23 displays 10× magnification birefringence images of V2 Gel.

FIG. 23 displays 10× magnification birefringence images of V2 Gel. The right image was taken with an optical microscope coupled with a linear polarizer. The right image was converted to a binary mask and overlaid over a brightfield image of the same location.

Example 24

Figure 24:
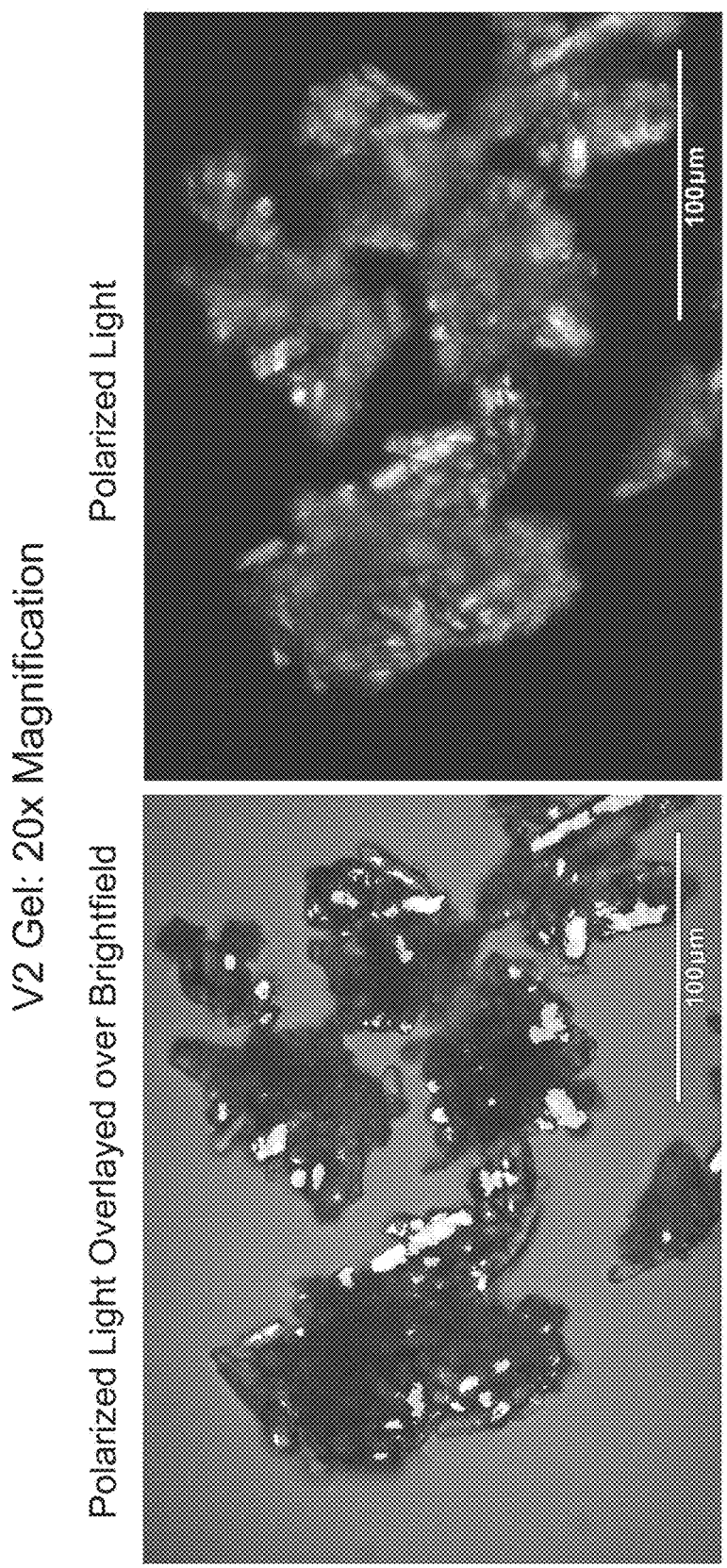
FIG. 24 displays 20× magnification birefringence images of V2 Gel.

FIG. 24 displays 20× magnification birefringence images of V2 Gel. The right image was taken with an optical microscope coupled with a linear polarizer. The right image was converted to a binary mask and overlaid over a brightfield image of the same location. The green areas represent particles with birefringence properties.

Example 25

In another example, Alkaline phosphatase (ALP) functional activity was determined from C2C12 cell cultures incubated in the presence of HCT/P R-14 (Stability Biologics) and OsteoAmp Putty (Advanced Biologics). HCT/P R-14 was also compared to rhBMP2 purified protein or to Infuse Bone Graft (Medtronic). ALP was determined after 6 and 13 days of cell culture using a colorimetric assay and results were compared among samples. After 6 days, no statistical difference in ALP activity from HCT/P R-14 and OsteoAmp treated C2C12 was observed. After 13 days, HCT/P R-14 stimulated ALP activity that was significantly greater than OsteoAmp-treated cells on a per mass basis. Specifically, HCT/P R-14 (12 mg/mL) stimulated a 1.7-fold increase in ALP activity that was significantly greater then ALP activity stimulated by OsteoAmp (12 mg/mL) that was 1.1-fold greater than vehicle (i.e., water)-treated cells. All cell culture and assay reagents were obtained from common commercial suppliers and were of molecular biology grade.

R-14 and OsteoAmp HCT/Ps were compared on a mass basis. Each HCT/P was accurately weighed into sterile microcentrifuge tubes and transferred to 12-well tissue culture plates correcting for residual mass of HCT/P in the tubes following transfer to the plate. An average of 3 mg and 12 mg were used in each HCT/P treatment group to test dose-dependency of effects. R-14 and Infuse were compared on a volume basis. The Infuse Collagen Sponge was cut with a sterile blade to a 0.05 cc volume. The lyophilized rhBMP2 powder that comes with the kit (4.2 mg rhBMP2) was reconstituted in sterile water (3.2 mL) to give a 1.3 mg/mL solution of rhBMP2 according to the manufacturer's instructions. A dilution series of the rhBMP2 stock was also prepared by serial 100-fold dilutions into sterile water with the final concentration series: 1300 ug/mL (full dose), 13 ug/mL, 0.13 ug/mL and 0.0013 ug/mL. A 0.050 mL aliquot of each solution was added to 0.05 cc of the Absorbable Collagen Sponge to deliver a mass of BMP2 to each well of: 66,600 ng, 666 ng, 6.66 ng and 0.0666 ng. The reconstituted Infuse was let stand for 15 minutes before carefully placing in 12-well cell culture dishes ensuring that the sponge was handled delicately.

A solution of purified recombinant human BMP2 protein (eBioscience) was prepared as a 5 ug/mL solution in sterile water. A 20 µL aliquot was added to media (1 mL, as below) to deliver a final BMP2 concentration of 100 ng/mL in cell culture. All of the above samples were prepared and tested in triplicate. 1 mL of media (DMEM+10% FBS) was added to each well containing HCT/P, Infuse or BMP2 solution aliquot immediately before addition of the cells, below. C2C12 cells previously expanded in a T-175 flask were harvested with 0.05% Trypsin, centrifuged (1200 rpm for 3 min.), washed with dPBS and centrifuged (3×), then re-suspended in media. Aliquots of this C2C12 cell suspension were added to each well to give an initial plating density of 4,000 cells/well and the plates were incubated in a 5% CO2 incubator at 37° C. One-half of the media was exchanged every 3 days will a fresh aliquot of media.

ALP activity was determined in C2C12 cells after 6 days and 13 days by adapting a method we previously described (1). At each time point, media was decanted from the cells and the cells were washed with dPBS (3×1 mL) and aspirated. 400 µL of ALP buffer (i.e., 10 mM Tris at pH 8.0 with 15 mM saline, containing 0.5% wt/wt Triton X-100, 1 mM MgCl2, 5 µM ZnCl2) was added to each well. Plates were placed on a horizontal orbital shaker for 10 minutes at 300 rpm. Cells were further lysed by gently passing the supernatant through a pipet tip multiple times while avoiding foaming of the samples, and then the supernatant was transferred to fresh microcentrifuge tubes kept at 4° C. Samples were centrifuged at 3500 rpm for 3 minutes at 4° C. 50 =L aliquots of each sample or p-nitrophenol standard solution series (800, 400, 200, 100, 50, 25, 12.5, 6.12 and 0 ug/mL) were transferred to a 96-well plate for analysis. To each well was added 100 µL of a 2 mg/mL solution of p-nitrophenylphosphate in water. The plate was incubated at 37° C. for 1.5 h. At this time, 100 µL of stop solution (10 mM Tris containing 1 mM EDTA with pH adjusted to 10 with NaOH solution) was added to each well and the absorbance at 405 nm was immediately read on a plate reader.

Protein concentration in the ALP cell lysis supernatants was determined using the BCA assay (2). Aliquots (25 µL) of the protein extracts were added to a 96 well plate in triplicate along with a concentration series of bovine serum albumin protein standard (OmniPure, Fraction 5) prepared in ALP assay buffer (above). BCA working reagent (200 µL, Pierce) was added to each well containing sample or calibration standard and the plate incubated at 37° C. for 30 minutes. The plate was allowed to cool to ambient temperature over 10 minutes and then the absorbance at 560 nm was determined.

ALP functional activity was determined on a protein-normalized basis by dividing the A405 (i.e., ALP product) measurements by the A560 measurements for BCA protein determination on a per sample basis. Absorbance measurements for either assay were within the bounds of the product standard curve or otherwise diluted if the absorbance measurements were too high. ALP activity was expressed as fold-change in ALP activity compared to vehicle (i.e., water)-treated cells at day 6 and day 13 independently. Sample replicates (n=3) were averaged and standard deviation/standard error was determined. Statistical comparisons were made by ANOVA using a Bonferroni post-hoc test for multiple comparisons.

ALP functional activity determined on day 6 of C2C12 incubation was low in all treatment groups containing HCT/Ps. At any concentration tested, HCT/P R-14 did not provide a statistical difference in ALP activity compared to vehicle (i.e., water)-treated cells on day 6. Compared to vehicle-treated cells, OsteoAmp (3 mg/mL) provided a 1.4-fold increase in ALP activity on day 6 that was significant (p<0.05). However at higher concentration of OsteoAmp (12 mg/mL), the effect of the HCT/P on ALP activity was mitigated and not statistically different than vehicle (i.e., water)-treated cells. Indeed, comparison of ALP activity stimulated by R-14 and OsteoAmp showed no statistical difference among the HCT/Ps at either concentration on day 6. rhBMP2 (100 ng/mL)-treated cells that were used as a positive control showed a 1.4-fold increase in ALP activity that was significantly greater than vehicle-treated cells that supported that increased ALP could be observed at this early time point at sufficiently high concentrations of BMP2.

The results with ALP activity measurements were considerably different on day 13 of C2C12 incubation compared to day 6. Stability Biologics' HCT/P R-14 showed a dose-dependent increase in ALP activity that reached a 2.2-fold increase at 66 mg/mL compared to vehicle-treated cells on day 13. At all concentrations, R-14 stimulated greater ALP activity on day 13 greater than the values observed for R-14 on day 6 compared to vehicle-treated cells. HCT/P R-14 was compared to OsteoAmp at 2 concentrations: 3 mg/mL and 12 mg/mL. Stability Biologics' HCT/P R-14 gave a significantly greater induction of ALP activity than OsteoAmp on a per mass basis. At 3 mg/mL, the R-14 treated cells gave a 1.2-fold increase in ALP compared to OsteoAmp treated cells that were unchanged from vehicle-treated cells (i.e., 1.0-fold). At 12 mg/mL, the Stability Biologics' R-14 HCT/P gave a 1.7-fold increase in ALP activity compared to a 1.1-fold increase in ALP activity for OsteoAmp that was a significant difference (p<0.05). On day 13, BMP2 (100 ng/mL) gave a 1.3-fold increase in ALP activity that was similar to its day 6 value. Thus, on day 13 the Stability Biologics' HCT/P (12 mg/mL) exceeded the effect of 100 ng/mL BMP2 on stimulating C2C12 ALP activity by 31%. FIG. 34A, B. ALP activity determined in C2C12 cell cultures incubated in the presence of HCT/P R-14 or OsteoAmp or purified rhBMP2 protein solution. ALP activity was normalized to vehicle (i.e., water)-treated cells on days 6 and 13 independently. A. ALP activity determined on day 6. B. ALP activity determined on day 13. Results are averaged quality bone cell growth may be an advantage. Calcium deposition was apparent by light microscopy in the plate wells that was consistent with osteogenic differentiation of these cells, as we've described before. Also, cell morphology changes were consistent with the formation non-myoblasts by the appearance of smaller cells that tended to be rounder in appearance rather than oblong cells, particularly as cells approached confluence.

TABLE 1

Tabulated Data for ALP activity from C2C12 cells treated with HCT/Ps, rhBMP2 or Infuse. Data relative to vehicle-treated cells on days 6 or 13 separately.

| Sample | Day 6 Average ALP Activity (Fold-Change) n = 3 | Standard Error of the Mean | Day 13 Average ALP Activity (Fold-Change) n = 3 | Standard Error of the Mean |
| --- | --- | --- | --- | --- |
| R-14 (3 mg/mL) | 1.1 | 0.2 | 1.2 | 0.09 |
| R-14 (12 mg/mL) | 1.1 | 0.1 | 1.7 | 0.4 |
| R-16 (66 mg/mL, 0.05 cc) | 0.8 | 0.02 | 2.2 | 0.2 |
| OsteoAmp (3 mg/mL) | 1.4 | 0.1 | 1.0 | 0.02 |
| OsteoAmp (12 mg/mL) | 1.2 | 0.1 | 1.1 | 0.04 |
| BMP2 (100 mg/mL) | 1.4 | 0.06 | 1.3 | 0.3 |
| Infuse - 0.066 ng | 1.0 | 0.3 | 2.4 | 1.6 |
| Infuse - 6.6 ng | n/d | n/d | 5.2 | 0.4 |
| Infuse - 666 ng | 0.8 | 0.06 | 125 | 22 |
| Infuse - 66,000 ng (full dose) | 1.5 | 0.3 | 60 | 0.8 | values of independent replicates (n=3) showing error bars for standard error of the mean. * p<0.05

ALP activity determined on day 6 was low in all treatment groups. At any concentration tested, HCT/P R-14 did not provide a statistical difference in ALP activity compared than vehicle-treated cells on day 6. Only Infuse full dose (66,000 ng/mL) provided an increase in ALP activity on day 6 of C2C12 incubation that approached statistical significance (p<0.1).

Figure 35A:
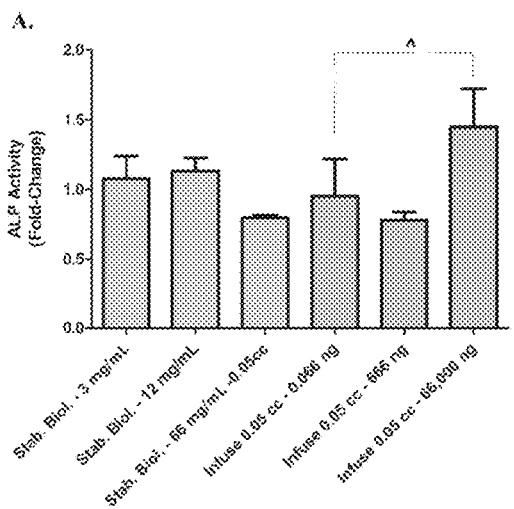
FIG. 35A, B are graphs showing ALP activity.
Figure 35B:
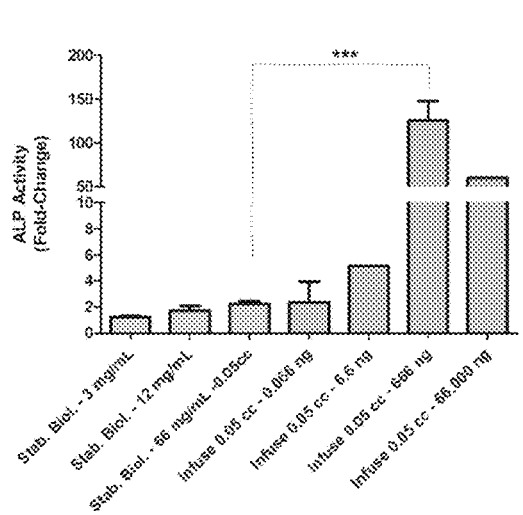
Figure 36A:
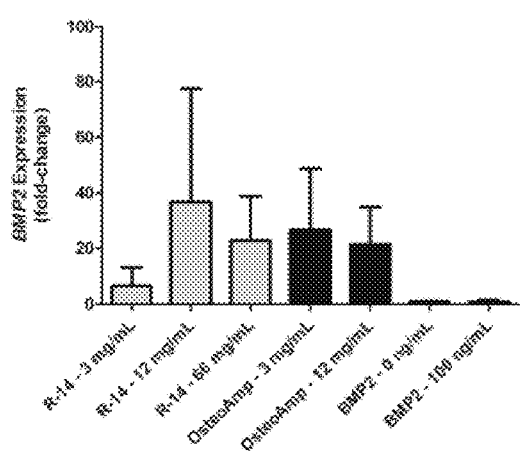
FIG. 36A, B, C, D are graphs showing BMP2 and ALP expression levels.
Figure 36B:
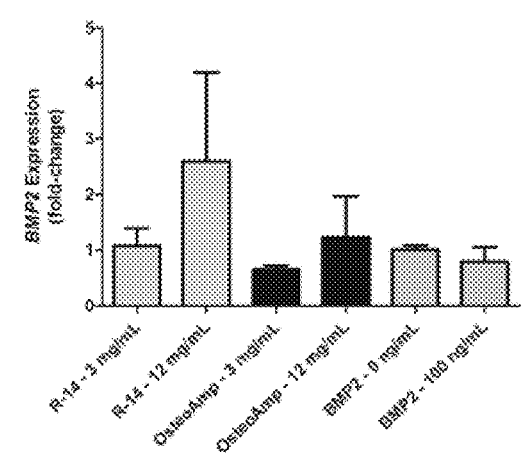
Figure 36C:
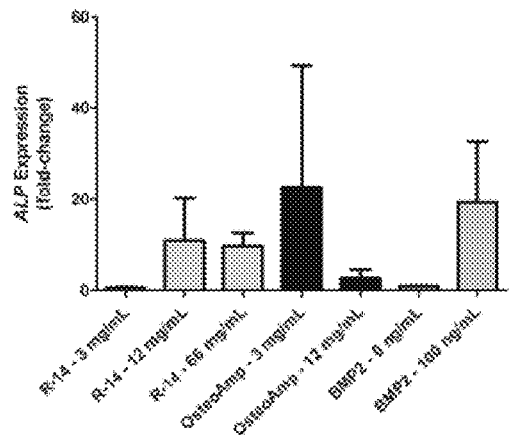
Figure 36D:
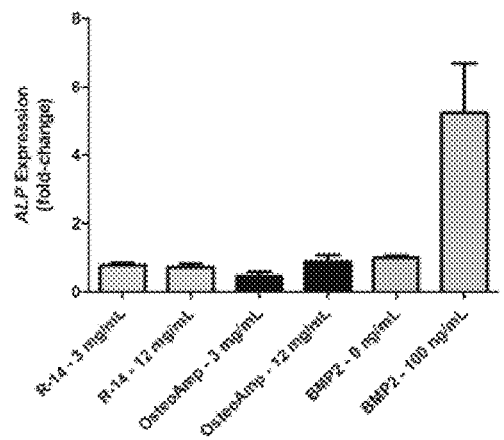
Figure 37A:
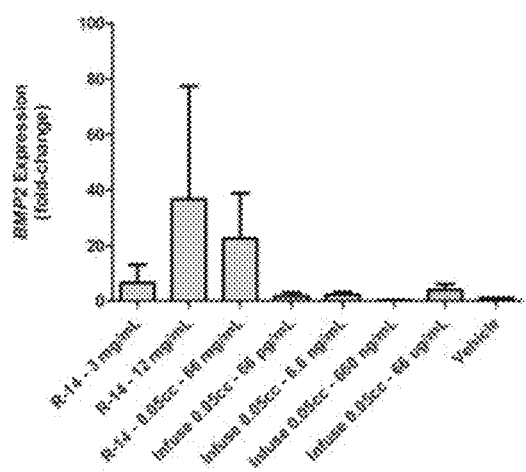
FIG. 37A, B, C, D are graphs showing BMP2 and ALP expression levels.
Figure 37B:
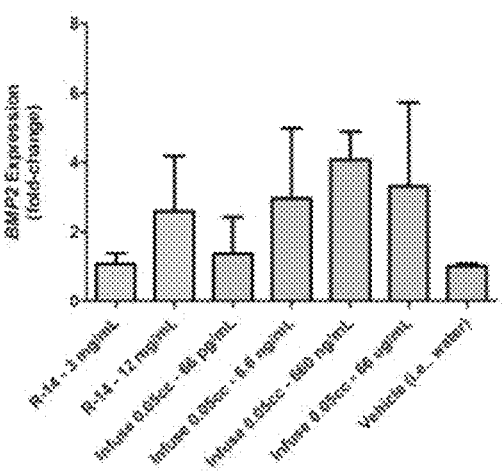
Figure 37C:
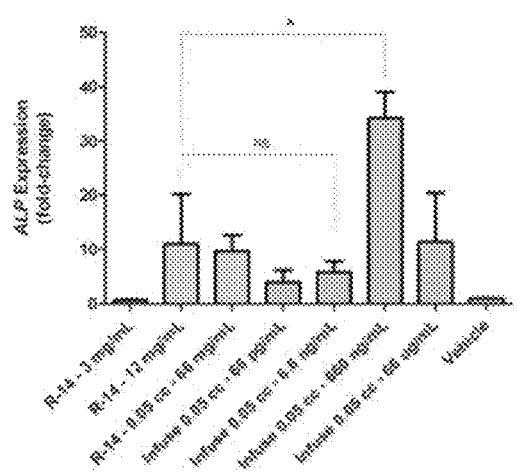
Figure 37D:
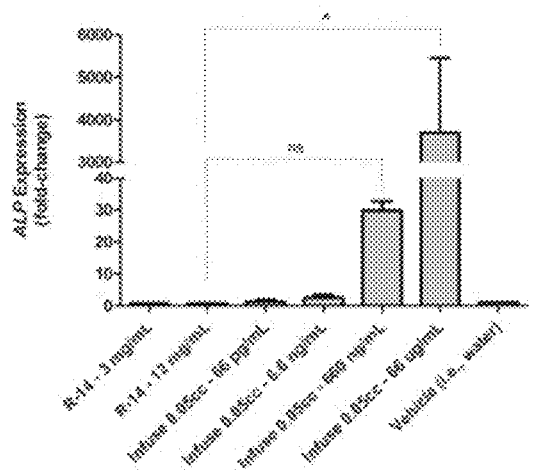

The results with ALP activity measurements were considerably different on day 13 of C2C12 incubation compared to day 6. ALP activity stimulated by Infuse was much greater on day 13 than observed on day 6. Infuse also stimulated much greater ALP activity than in R-14 HCT/P-treated C2C12 cells. A 0.05 cc dose of R-14 stimulated a 2.2-fold increase in ALP activity on day 13 that not statistically different from 0.05 cc Infuse with 0.066 ng BMP2 (n.b., this is a million-fold dilution from 'full-dose' Infuse BMP2). Infuse gave a dose-dependent increase in ALP activity at 6.6 ng (5.2-fold) and 666 ng (125-fold) that was actually slightly diminished at the Infuse full dose (i.e., only 60-fold at 66,000 ng BMP2). FIG. 35A, B. ALP activity determined in C2C12 cell cultures incubated in the presence of R-14 or an Infuse dose-range of BMP2. ALP activity was normalized to vehicle (i.e., water)-treated cells on days 6 and 13 independently. A. ALP activity determined on day 6. B. ALP activity determined on day 13. Results are averaged values of independent replicates (n=3) showing error bars for standard error of the mean. ^p<0.1, *** p<0.001

Cell growth rate in the presence of HCT/Ps versus Infuse was markedly different. Cells treated with Infuse grew much faster and this was apparent even after 6 days of incubation. Cells treated with HCT/Ps grew slower than Infuse and cell growth appeared to be slower as the concentration of HCT/Ps increased judged by visual inspection under a light microscope. But cell proliferation per se may not lead to high yield of high-quality bone cells. Thus, slower, higher Example 26

In yet another example, Bone Morphogenetic Protein 2 and Alkaline Phosphatase gene expression levels were determined from C2C12 cell cultures incubated in the presence of R-14 (Stability Biologics) and OsteoAmp (Advanced Biologics). R-14 was also compared to rhBMP2 purified protein or to Infuse Bone Graft (Medtronic). Gene expression levels were determined after 6 and 13 days of cell culture using qPCR and results compared among samples. Stability Biologics' R-14 provided a marked increase in BMP2 and ALP expression in C2C12 cell cultures that was particularly prominent in the early incubation periods determined on day 6 of treatment. On day 6, R-14 (12 mg/mL) gave a 37-fold increase in BMP2 expression and an 11-fold increase in ALP expression compared to vehicle (i.e., water)-treated cells. R-14 at 12 mg/mL showed a non-significant trend to increase BMP2 and ALP expression greater than OsteoAmp on a per mass basis.

R-14 and OsteoAmp were compared on a mass basis. Each sample was accurately weighed into sterile microcentrifuge tubes and transferred to 12-well tissue culture plates correcting for residual mass in the tubes following transfer to the plate. An average of 3 mg and 12 mg were used in each treatment group to test dose-dependency of effects. R-14 and Infuse were compared on a volume basis. The Infuse Collagen Sponge was cut with a sterile blade to a 0.05 cc volume. The lyophilized rhBMP2 powder that comes with the kit (4.2 mg rhBMP2) was reconstituted in sterile water (3.2 mL) to give a 1.3 mg/mL solution of rhBMP2 according to the manufacturer's instructions. A dilution series of the rhBMP2 stock was also prepared by serial 100-fold dilutions into sterile water with the final concentration series: 1300 ug/mL (full dose), 13 ug/mL, 0.13 ug/mL and 0.0013 ug/mL. A 0.050 mL aliquot of each solution was added to 0.05 cc of the Absorbable Collagen Sponge to deliver a mass of BMP2 to each well of: 66,600 ng, 666 ng, 6.66 ng and 0.0666 ng.

The reconstituted Infuse was let stand for 15 minutes before carefully placing in 12-well cell culture dishes ensuring that the sponge was handled delicately. A solution of purified recombinant human BMP2 protein (eBioscience) was prepared as a 5 ug/mL solution in sterile water. A 20 μL aliquot was added to media (1 mL, as below) to deliver a final BMP2 concentration of 100 ng/mL in cell culture.

C2C12 cells previously expanded in a T-175 flask were harvested with 0.05% Trypsin, centrifuged (1200 rpm for 3 min.), washed with dPBS and centrifuged (3×), then resuspended in media. Aliquots of this C2C12 cell suspension were added to each well to give an initial plating density of 4,000 cells/well and the plates were incubated in a 5% CO2 incubator at 37° C. One-half of the media was exchanged every 3 days will a fresh aliquot of media.

Target gene expression was determined in C2C12 cells after 6 days and 13 days by adapting a method we previously described (1). At each time point, media was decanted from the cells and Trizol (0.4 ml/well, Life Technologies) was added and the plates were periodically agitated over 15 minutes at room temperature. The Trizol cell extracts were gently lysed by passing the supernatant through a pipet tip multiple times while avoiding foaming of the samples, and then the supernatant was transferred to fresh microcentrifuge tubes held at 0° C. RNA isolation was based on the manufacturer's recommendations. Chloroform (0.2 mL/tube) was added to each microcentrifuge tube containing Trizol cell extract and the tubes shaken by hand for 20 s. Microcentrifuge tubes were left to stand for 5 minutes, then centrifuged at 12000 rcf for 15 minutes at 4° C. Upon visual confirmation of separation of the layers, approximately 200 uL aliquots were taken from the top clear aqueous layer of each tube and transferred to fresh microcentrifuge tubes. Isopropanol (200 μL) was added to each tube and let stand for 10 minutes at ambient temperature. Tubes were centrifuged at 12000 rcf for 10 minutes at 4° C. Upon visual confirmation of an RNA pellet, the supernatant was carefully decanted by pipet. To each tube, a 400 μL aliquot of 75% ethanol was added and the samples vortexed then centrifuged at 7500 rcf for 5 minutes at 4° C. The supernatant was carefully decanted from the RNA pellet by pipet and the pellet was air-dried in a tissue-culture hood for 10 minutes before reconstitution in molecular biology grade water (40 μL/tube). Samples were placed in a heating block at 60° C. for 15 minutes. Upon completion, RNA concentration and purity (i.e., $A_{260}/A_{280}$) was determined on a Nanodrop in accord with MIQE guidelines (2).

cDNA was prepared using the BioRad iScript cDNA Synthesis Kit following manufacturer's instructions. Each cDNA preparation corresponding to an RNA extract was prepared in sterile 200 μL PCR tubes. Each tube received: 500 ng of total RNA, 1 μL of Reverse Transcriptase solution, 4 μL of iScript Reaction Mixture and sufficient water to provide a 20 μL total reaction volume. cDNA synthesis was done on a BioRad DNA engine with the following settings: 25° C. for 5 minutes, 42° C. for 30 minutes then 85° C. for 5 minutes. Upon completion, each sample was diluted ⅒ with molecular biology grade water and samples were maintained at 4° C. or less.

qPCR was conducted using the BioRad iQ SYBR Green Supermix with a Bio-Rad iQ5 thermocycler (Bio-Rad) under the following conditions: 95° C., 2 min; 95° C., 10 s and 60° C., 45 s for 40 cycles; and then 60° C. for 71 cycles for a melt curve. Samples were prepared by combining 6 μL of cDNA solution, 7 μL of the SYBR Green reagent and 0.5 μL each of forward and reverse primers, and the plate was briefly centrifuged (5 min at 1200 rpm) before analysis. 18 s rRNA was used as reference gene. Forward and reverse primers used in qPCR were as follows

| Gene Target | Forward Primer | Reverse Primer | Amplicon Length |
|---|---|---|---|
| mBMP2 | 5'-GGGACCCGCTGTCTTCTAGT-3' (SEQ ID NO: 1) | 5'-TCAACTCAAATTCGCTGAGGAC-3' (SEQ ID NO: 2) | 154 |
| mALP | 5'-AACCCAGACACAAGCATTCC-3' (SEQ ID NO: 3) | 5'-GAGAGCGAAGGGTCAGTCAG-3' (SEQ ID NO: 4) | 151 |
| 18SRNA | 5'-CTCAACACGGGAAACCTCAC-3' (SEQ ID NO: 5) | 5'-CGCTCCACCAACTAAGAACG-3' (SEQ ID NO: 6) | 109 | qPCR data was analyzed by the ΔΔCt method (3). Each experimental condition was determined by independent replicates (n=3) and then the average and standard deviation/standard error was determined. Results were expressed as the fold-change in gene expression and data were normalized to vehicle (i.e., water)-treated cells on day 6 or day 13. Statistical comparisons were made by ANOVA using a Bonferroni post-hoc test for multiple comparisons.

A marked induction of osteogenic target genes was observed in all treatment groups on day 6 (Table 4). On day 6, R-14 gave a dose-dependent increase in BMP2 and ALP expression between 3 and 12 mg/mL, but no further increase was observed at 66 mg/mL. R-14 at 12 mg/mL gave a 37-fold increase in BMP2 expression and an 11-fold increase in ALP expression compared to vehicle (i.e., water)-treated cells. At the same dose of OsteoAmp (i.e., 12 mg/mL), a 21-fold increase in BMP2 expression and a 2.8-fold increase in ALP expression was observed. Despite the trend that R-14 provided greater induction of target genes compared to treatment with OsteoAmp (on day 6), statistical significance of these comparisons could not be achieved due to inherently high variability in the measurements. Both R-14 and OsteoAmp induced BMP2 expression greater than a single dose of BMP2 at 100 ng/mL that is a dose that has been shown to effect C2C12 differentiation (4).

On day 13 of C2C12 treatment, the magnitude of the differences in gene expression among treatment groups was generally diminished from inter-group comparisons on day 6, albeit direct comparison of gene expression levels between days was not possible in this experimental design. However, trends from day 6 were present. On day 13, R-14 (12 mg/mL) gave a 2.6-fold increase in BMP2 expression compared to day 13 vehicle-treated cells. At the same dose of OsteoAmp (12 mg/mL), a 1.2-fold increase in BMP2 expression was observed. Despite the trend that R-14 provided greater induction of BMP2 than OsteoAmp, statistical significance of these comparisons could not be achieved due to large variability in these measurements. RNA analysis on day 13 in the R-14 treatment group that received 66 mg/mL (0.05 cc) was not possible because the high concentration of substance interfered with recovery of RNA from cell culture. FIGS. 36 A-D show BMP2 and ALP expression levels determined in C2C12 cell cultures incubated in the presence of R-14, OsteoAmp or purified rhBMP2 protein. Gene expression was normalized to vehicle (i.e., water)-treated cells on days 6 and 13 independently. A. BMP2 expression on day 6. B. BMP2 expression on day 13. C. ALP expression on day 6. D. ALP expression on day 13. Results are average values of independent replicates (n=3) showing error bars for standard error of the mean.

The effect of R-14 on osteogenic target gene expression was compared to the effect of 0.05 cc of Infuse formulated with a dose-range of rhBMP2 (Table 5). On day 6 of treatment, 0.05 cc of R-14 (i.e., 66 mg/mL) gave a 23-fold increase in BMP2 expression that was markedly greater than treatment with 0.05 cc of Infuse at full dose (i.e., theoretically capable of delivering 66 ug/mL rhBMP2 into solution) which provided a 4.0-fold increase in BMP2 expression. R-14 at 0.05 cc increased ALP expression by 9.7-fold on day 6 that was comparable to the effect of 0.05 cc Infuse at full dose that gave an 11-fold increase on ALP. Despite the trend that R-14 gave greater induction of BMP2 on day 6 of treatment than Infuse, statistical significance in these comparisons could not be achieved due to inherently high variability in the measurements. FIGS. 37A-D show BMP2 and ALP expression levels determined in C2C12 cell cultures incubated in the presence of R-14 and an Infuse dose-range of BMP2. Gene expression was normalized to vehicle (i.e., water)-treated cells on days 6 and 13 independently. A. BMP2 expression on day 6. B. BMP2 expression on day 13. C. ALP expression on day 6. D. ALP expression on day 13. Results are averaged values of independent replicates (n=3) showing error bars for standard error of the mean. ^p<0.10, ns=not significant (i.e., p>0.10)

On day 13 of C2C12 treatment, RNA analysis of the R-14 treatment group that received 0.05 cc (i.e., 66 mg/mL) was not possible because the high concentration of substance interfered with recovery of RNA from cell culture. Comparisons were made to R-14 at 12 mg/mL to the Infuse dose-range. Even at this lower concentration, R-14 stimulated a 2.6-fold increase in BMP2 expression that could not be statistically distinguished than the effect of Infuse at full dose (i.e., 66 ug/mL) that gave a 3.3-fold increase in BMP2 expression. However, Infuse did increase ALP expression on day 13 greater than the effect of R-14. Infuse at 666 ng/mL gave a 34-fold induction of ALP expression, although this increase was not statistically distinguished from R-14 treatment. At full dose Infuse, a significant difference to R-14 was found (p<0.10).

Results from this study showed that Stability Biologics' R-14 stimulated a marked increase in BMP2 and ALP expression with a trend showing that the induction with R-14 was greater than the effect of OsteoAmp on these genes. One of the interesting results was that the effect of the samples (i.e., either R-14 or OsteoAmp) on stimulating osteogenic gene expression was greater on day 6 than most of the positive control treatment groups: BMP2 at 100 ng/mL or Infuse dose range. This difference was mitigated over time and by day 13 there was much less difference in the magnitude of gene expression between R-14, OsteoAmp and the positive control groups, or in some cases the positive control groups gave significantly greater gene induction than the experimental samples. Of course there may be several reasons for this effect, but burst release kinetics of a 'growth factor cocktail' from R-14 or OsteoAmp presents an intriguing possibility that could explain a significant induction of osteogenic target genes. As the growth factors are diluted from the media over time (i.e., with media exchanges) this effect would be gradually lost. Surprisingly, Infuse that is essentially soaked with a concentrated BMP2 solution did not have a major effect on day 6 and required greater time for the effect on osteogenic target genes to be observed. However, on day 13 the large amounts of BMP2 that were present in Infuse were manifested as very large increases in ALP expression exceeding 100-fold at some concentrations. Comparing these very different substances is inherently difficult due to the different nature of the materials, the different adsorption and release kinetics of growth factors that are expected and the very large exogenous concentration of BMP2 added to the collagen scaffold in the Infuse product. Nonetheless, the results generally support that R-14 stimulated osteogenic differentiation of the cells very effectively during short in vitro incubations.

TABLE 2

Tabulated Data for BMP2 Expression from C2C12 cells treated with R-14, OsteoAmp, rhBMP2 or Infuse. Data relative to vehicle-treated cells on days 6 or 13 separately.

| Sample | Day 6 Average BMP2 Expression (Fold-Change) n = 3 | Standard Error of the Mean | Day 13 Average BMP2 Expression (Fold-Change) n = 3 | Standard Error of the Mean |
|---|---|---|---|---|
| R-14 (3 mg/mL) | 6.6 | 6.5 | 1.07 | 0.32 |
| R-14 (12 mg/mL) | 37 | 41 | 2.59 | 1.6 |
| R-16 (66 mg/mL, 0.05 cc) | 23 | 16 | Not determined | |
| OsteoAmp (3 mg/mL) | 27 | 22 | 0.65 | 0.070 |
| OsteoAmp (12 mg/mL) | 21 | 14 | 1.22 | 0.75 |
| BMP2 (100 ng/mL) | 0.90 | 0.60 | 0.79 | 0.26 |
| Infuse - 66 pg | 1.7 | 1.4 | 1.36 | 1.1 |
| Infuse - 6.6 ng | 2.2 | 1.1 | 2.96 | 2.0 |
| Infuse - 666 ng | 0.30 | 0.10 | 4.07 | 0.8 |
| Infuse - 66,000 ng (full dose) | 4.0 | 2.2 | 3.32 | 2.4 |

TABLE 3

Tabulated Data for ALP Expression from C2C12 cells treated with R-14, OsteoAmp, rhBMP2 or Infuse. Data relative to vehicle-treated cells on days 6 or 13 separately.

| Sample | Day 6 Average ALP Expression (Fold-Change) n = 3 | Standard Error of the Mean | Day 13 Average ALP Expression (Fold-Change) n = 3 | Standard Error of the Mean |
|---|---|---|---|---|
| R-14 (3 mg/mL) | 0.70 | 0.10 | 0.77 | 0.080 |
| R-14 (12 mg/mL) | 11 | 9.2 | 0.72 | 0.11 |
| R-16 (66 mg/mL, 0.05 cc) | 9.7 | 3.0 | Not determined | |
| OsteoAmp (3 mg/mL) | 23 | 27 | 0.46 | 0.13 |
| OsteoAmp (12 mg/mL) | 2.8 | 1.8 | 0.88 | 0.19 |
| BMP2 (100 ng/mL) | 19 | 13 | 5.2 | 1.5 |
| Infuse - 0.066 ng | 3.9 | 2.3 | 1.3 | 0.59 |
| Infuse - 6.6 ng | 5.8 | 2.0 | 2.4 | 0.99 |
| Infuse - 666 ng | 34 | 4.8 | 30. | 2.9 |
| Infuse - 66,000 ng (full dose) | 11 | 9.0 | 3700 | 1800 |

Example 27

In another example an osteoinductive bone graft composition material is prepared by first heating a premeasured quantity of a mineral acid in a vessel to a suitable temperature, while stirring at a predetermined stir rate or at least 200 rpm. In other examples, the stir rate is at least 600 rpm and at least 1000 rpm. In still other examples, the stir rate is sufficient to create a shear rate of at least $7\times10^{-5}$ $s^{-1}$. The mineral acid in this particular example is 1N HCL. In other examples, HCL concentrations of about 0.1N to about 2N may be used. In still other examples, mineral acids other than HCL could be used. The mineral acid is heated to about 55° C. In other examples, the mineral acid may be heated to about 45° C. to about 60° C.

Bone powder is then added to the heated mineral acid and the reaction vessel is closed. The wt. to vol. ratio of bone powder to mineral acid is about 1/20 to about 2/5. The reaction mixture is maintained at the desired temperature and continuously stirred for about 0.5 to about 3 hours. At the end of the reaction time the resultant bone matrix material is separated from the liquid portion of the reaction vessel using known separation methods.

Example 28

In still another example a bone matrix material is prepared by heating a premeasured quantity of a mineral acid in a vessel to a suitable temperature while stirring at a high shear rate. The mineral acid in this particular example is 1N HCL. In other examples, HCL concentrations of about 0.1N to about 2N may be used. In still other examples, mineral acids other than HCL could be used. In this example the stir rate is at least 200 rpm. In other examples, the stir rate is at least 600 rpm and at least 1000 rpm. In still other examples, the stir rate is sufficient to create a shear rate of at least $2\times10^{-4}$ $s^{-1}$. The mineral acid is heated to about 55° C. In other examples, the mineral acid may be heated to about 45° C. to about 60° C.

Bone powder is then added to the heated mineral acid and the reaction vessel is closed while continuously stirring the admixture at the predetermined stir rate. The wt. to vol. ratio of bone powder to mineral acid is about 1/20. In other examples, the wt. to vol. ratio about bone powder to mineral acid may be up to about 2/5. The stir rate and temperature of the reaction vessel are maintained for a sufficient period of time, typically about 0.5 hours to about 3 hours. At the end of the reaction time the resultant bone matrix material is separated from the liquid portion of the reaction vessel.

In this particular example separation and isolation of the resultant demineralized bone matrix is carried out by a further process of removing off the supernatant liquid and adding a sufficient quantity of deionized or distilled water to dissolve any salts that may have formed during the addition of a buffer. Any supernatant liquid resulting from the addition of the water is then removed to yield a residual material. This residual material is then transferred to one or more drying trays with the aid of a solvent, such as a suitable ketone, if desired. The solvent (if any) is then evaporated, the residual material mixed to form a homogeneous mixture, and the resulting homogeneous material allowed to cool.

Alternatively, the separating and isolating of the resultant demineralized bone matrix is carried out using a different method. In this example an admixture comprising a buffer and the demineralized bone material is poured into centrifuge bottles. The bottles are then centrifuged for a suitable period of time to separate the demineralized bone material from any liquid. The liquid is decanted and the demineralized bone can then be rinsed with water, acetone, or both. The rinsed demineralized bone material is then dried in drying trays and mixed to form a homogeneous mixture.

Example 29

Any of the previously described osteoinductive bone graft compositions may be packaged for distribution in the form of a kit. One such example of a kit comprises one or more syringes pre-filled with a premeasured quantity of the osteoinductive bone graft composition enclosed in suitable packaging under sterile conditions. In one example, the osteoinductive bone graft composition is in the form of a powder until sufficient shear stress is applied such as by depressing the syringe plunger and expelling the bone graft from the syringe. In other examples, the osteoinductive bone graft composition is in the form of a liquid or a putty until sufficient shear stress is applied.

OsteoAMP® is a registered trademark of Advanced Biologics, LLC, 25 Pacifica Irvine, Calif. 92618. Sterifuse® is a registered trademark of Transplant Technologies of Texas Ltd. TTT, LLC, 4808 Research Dr. San Antonio, Tex. 78240. Instatherm® is a registered trademark of Ace Glass, Inc., P.O. Box 688, 1430 North West Blvd., Vineland, N.J.

08362-0688. J-KEM® is a registered trademark of J-KEM electronics, Inc., 6970 Olive Blvd., St, Louis, Mo. 63017.

While the disclosure has been illustrated and described in detail in the figures and foregoing description, the same is to be considered as illustrative and not restrictive in character, it being understood that only selected embodiments have been shown and described, and that all changes, modifications and equivalents that come within the spirit of the disclosures described heretofore and/or defined by the following claims are desired to be protected, including any variations, uses, or adaptations that follow the general principles herein, and such departures as come within known or customary practice within the art to which the present disclosure pertains. In addition, all publications cited herein are indicative of the level of skill in the art, and are hereby incorporated by reference in their entirety as if each had been individually incorporated by reference and fully set forth.

What is claimed is:

1. A bone matrix composition consisting of:
bone powder;
brushite particles; and
monetite particles;
wherein the bone powder, brushite particles, and monetite particles are combined to yield an admixture;
wherein the bone powder, brushite, and monetite are derived from bone;
wherein application of shear force to the admixture yields a self-binding putty;
wherein the self-binding putty exhibits sufficient wet-field integrity to be non-sticky and to resist degradation during lavage; and
wherein the self-binding putty exhibits decreasing viscosity with increased application of shear force; and
wherein the admixture is 16-50% by weight monetite and 16-80% by weight brushite.

2. The bone matrix composition of claim 1, wherein the ratio of brushite to monetite present is from about 2.2 to about 0.25.

3. The bone matrix composition of claim 1, wherein the bone matrix composition contains less than 8 volume percent calcium.

4. The bone matrix composition of claim 1, wherein the bone powder is demineralized.

5. The bone matrix composition of claim 1, wherein the admixture particle size ranges from 200 microns to 800 microns.

6. A bone matrix composition consisting of:
bone powder;
brushite particles; and
monetite particles;
wherein the composition includes a physiological compilation of bioavailable growth factors;
wherein the bone powder, brushite particles, and monetite particles are combined to yield an admixture;
wherein the bone powder, brushite, and monetite are derived from bone;
wherein application of shear force to the admixture yields a self-binding putty;
wherein the self-binding putty exhibits sufficient wet-field integrity to be non-sticky and to resist degradation during lavage; and
wherein the self-binding putty exhibits decreasing viscosity with increased application of shear force; and
wherein the admixture is 16-50% by weight monetite and 16-80% by weight brushite.

7. The bone matrix composition of claim 6, wherein the physiologic compilation of bioavailable growth factors includes bone morphogenic proteins.

8. The bone matrix composition of claim 7, wherein the bone morphogenic proteins are selected from the group comprising BMP-2, BMP-4, BMP-7, VEGF, and combinations thereof.

9. A bone matrix composition, consisting of:
an organic phase; and
a particulate mineral phase, consisting of:
16-50% by weight monetite;
16-80% by weight brushite;
hydroxyapatite;
wherein the particulate mineral phase comprises 46-74% by weight of the bone matrix.

10. The bone matrix composition of claim 9, wherein the application of shear force to the composition converts the composition from a powder to a putty.

11. The bone matrix composition of claim 10, wherein the composition is a putty after sufficient shear stress is applied.

12. The bone matrix composition of claim 9, wherein the particle size range of the particulate mineral phase is from 200 microns to 800 microns.

13. A human bone matrix composition consisting of:
demineralized bone matrix containing both monetite and brushite;
wherein said composition maintains osteoinductive, osteoconductive, and osteogenic properties;
wherein said composition is a putty that exhibits wet field integrity including self-binding;
and wherein the composition is 16-50% by weight monetite and 16-80% by weight brushite.

* * * * *